(12) United States Patent
Kochinke

(10) Patent No.: US 7,074,426 B2
(45) Date of Patent: Jul. 11, 2006

(54) METHODS AND DRUG DELIVERY SYSTEMS FOR THE TREATMENT OF OROFACIAL DISEASES

(76) Inventor: Frank Kochinke, 3413 Antonacci Ct., San Jose, CA (US) 95148

( * ) Notice: Subject to any disclaimer, the term of this patent is extended or adjusted under 35 U.S.C. 154(b) by 640 days.

(21) Appl. No.: 10/113,730

(22) Filed: Mar. 27, 2002

(65) Prior Publication Data

US 2003/0185872 A1  Oct. 2, 2003

(51) Int. Cl.
*A61F 13/02* (2006.01)
(52) U.S. Cl. .................................................. 424/435
(58) Field of Classification Search ................ 424/435, 424/423
See application file for complete search history.

(56) References Cited

U.S. PATENT DOCUMENTS 6,386,869 B1   5/2002   Zegarelli

*Primary Examiner*—Carlos A. Azpuru
(74) *Attorney, Agent, or Firm*—Reed Intellectual Property Law Group

(57) ABSTRACT

This invention relates to methods of treating various orofacial diseases involving inflammation, infection and/or pain, using intratissue controlled release drug delivery systems. More particularly, the invention relates to methods for localized or targeted administration of a sustained release formulation of an agent such as an anti-inflammatory agent to a specified tissue location within the orofacial environment.

136 Claims, No Drawings

METHODS AND DRUG DELIVERY SYSTEMS FOR THE TREATMENT OF OROFACIAL DISEASES

FIELD OF THE INVENTION

This invention relates to methods of treating various diseases in or originating in the orofacial environment, using intratissue controlled release drug delivery systems. More particularly, the invention relates to methods for localized or targeted administration of a sustained release formulation to a specified tissue location within the orofacial environment, which includes the oral cavity, head and neck.

BACKGROUND OF THE INVENTION

There are several different drug delivery technologies that are utilized to treat disease. Conventional drug delivery methods typically result in the patient experiencing severe "peaks and valleys" in the plasma level of the therapeutic agent being administered, as well as often requiring multiple dosings per day.

These problems were addressed somewhat by the development of sustained release drug delivery products, where the patient experienced less severe plasma level "peaks and alleys" and there were reduced dosings per day. Subsequent development of controlled release drug delivery technologies provided for no "peaks and valleys" in the daily plasma level, as well as providing for a daily, weekly or monthly dosing regimen. Controlled release drug delivery systems can be designed to target a local area or the systemic circulation and can be administered in a variety of ways, including orally, transdermally, as an implant, by injections, and so forth.

Many methods of treating diseases in and originating in the orofacial environment, have involved oral administration of drugs such as anti-inflammatory or anti-infective agents, for example. However, such systemic therapies are often unable to reach the targeted diseased local area. In addition, patients can experience sub-therapeutic levels and/or fluctuating concentrations of agent with systemic therapies. Further, in order for such systemic administration to provide adequate drug levels to treat the orofacial tissue, the actual dosage administered often needs to be extremely high. As the systemic concentration is elevated, there is a greater likelihood of the patient experiencing systemic side-effects and even toxicity. Another problem with high-dosing therapies, particularly when administering anti-infective agents such as antibiotics, is the increase likelihood of bacterial resistance.

Other methods of treating orofacial diseases have involved topical applications and intra-oral products that are applied in the mouth or dental area on the surface of structures. Some formulations are placed within the periodontal pocket, others are on the mucous membrane or other surfaces, etc. Such formulations often include anti-infectives as it is often desirable to minimize or eliminate the bacteria present in the mouth while treating orofacial diseases such as periodontal disease. Examples of products that are positioned within the periodontal pocket include a tetracycline-containing ethylene/vinyl acetate copolymer that is positioned within the periodontal pocket (Actisite®, Proctor & Gamble); a chorhexidine gluconate-containing biodegradable hydrolyzed gelatin matrix (PerioChip®, Astra Pharmaceuticals); and a doxycycline-containing biodegradable polymer that is administered as a liquid and solidifies in situ to conform to the shape of the periodontal pocket (Atridox™, 8.5% doxycycline in the ATRIGEL® Delivery System, Atrix Laboratories, Inc.).

However, conventional and even the so-called advanced administration, including those involving the periodontal pocket have several limitations, ranging from low drug levels at the disease site and drug level fluctuation between applications to inconsistent patient compliance. And in the case of non-predetermined dosage forms, like for example the gel system, there is no assurance that any of the product has been placed properly into the pocket or spilled before or during application. Even when an attempt was made to place part of the product into the pocket, the dosage was not known. For these types of dosage forms there is no control over the accurate dosage amount and consequently over the delivery rate, negatively compounded by the fact that the final system can have variable shapes and surface areas, factors that critically influence drug delivery rates. In addition, besides being very clumsy to apply some products have to be manipulated before application (not ready-for-use right out of the storage system, e.g., multi-component systems that have to be mixed by the administrator before use) making the system prone to inappropriate handling, spilling and therefore having the potential for being non-therapeutic or not working as originally designed. But even when therapeutic agents are placed as directed within the oral cavity, the agent is subjected to wash-out or dilution due to the constant flow of saliva, crevicular fluid outflow from the periodontal pocket, as well as the patient's intake of food and beverages, all of which affect/minimize/reduce the amount of agent that is able to effectively treat the oral disease.

Another limitation with conventional administration is that the selection of therapeutic agents is somewhat limited to those that are less potent, to prevent toxicity. Based on thermodynamic reasons, very high systemic concentration levels (so high that they may cause systemic toxicity), are often required to drive the drug into the localized diseased area in an attempt to establish the therapeutic concentration level in the targeted tissue. Therefore, only therapeutic agents that have a large therapeutic index and are not too expensive, find utilization in conventional therapy. Active agents that may be more effective but are associated with toxicity or are very costly to administer in high doses, can not be used in the state of the art methodologies.

Accordingly, there is a continuing need to find improved methods for treating orofacial diseases that will overcome some or all of the shortcomings of the art, as well as present new methodologies for administering a wider range of therapeutic agents. The present invention addresses those needs by means of an implantable or insertable controlled release drug delivery system that is positioned within the diseased orofacial tissue and provides a uniform concentration of therapeutic agent at the target tissue site.

SUMMARY OF THE INVENTION

One aspect of the invention relates to a method of treating disease in or originating in the orofacial environment in a patient comprising the step of administering a drug delivery system within orofacial tissue, wherein the system comprises a semi-solid or solid depot and a therapeutically effective amount of at least one therapeutic agent contained therein, and is within the range of about 0.03–17 mm$^3$ in size.

Another aspect of the invention pertains to a method of treating disease in or originating in the orofacial environment in a patient comprising the step of administering a drug delivery system within orofacial tissue, wherein the system comprises a semi-solid or solid depot and a therapeutically effective amount of an anti-inflammatory agent contained therein.

Yet another aspect of the invention relates to a drug delivery system configured to be positioned within orofacial tissue comprising a semi-solid or solid depot and at least one therapeutic agent contained therein, and having a size within the range of about 0.03–17 mm$^3$.

Still another aspect of the invention is a drug delivery system configured to be positioned within orofacial tissue comprising a semi-solid or solid depot and about 35–4500 μg of a therapeutic agent contained therein, and having a size within the range of about 0.03–17 mm$^3$.

DETAILED DESCRIPTION OF THE INVENTION

The present invention comprises methods treating diseases in the orofacial environment orofacial diseases or diseases that originate in the orofacial environment and complications therefrom, by the intratissue administration of a controlled release drug delivery system to an orofacial site. The controlled release drug delivery systems used in the methods of the invention are suitable for use in administering one or more therapeutic agents at a predefined rate for periods of up to one month or longer. The agent(s) can be delivered directly to the target tissue or can be delivered to the nearby local vasculature or gland that in turn provides the means of carrying the agent to the desired target tissue location.

The controlled release drug delivery systems used in the methods are implantable or insertable systems comprised of a pre-manufactured small depot, having a therapeutic agent incorporated therein. Typically, the depot will be a biodegradable semi-solid or solid, but non-biodegradable applications are also contemplated. Exemplary materials and systems will be described in detail below as well as being described in the patents cited below.

The controlled release drug delivery systems used in the methods are small in size compared to existing products, which provides versatility in how and where they can be placed. Since these metered dosage systems provide for precise targeting of diseased tissue, smaller amounts of drug are needed than in conventional therapies. This provides several advantages in that a minute amount of drug can be delivered with maximum therapeutic benefit and minimum toxic side effects. This opens up an opportunity to deliver agents that are too costly or too toxic to deliver by traditional routes and methodologies.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive. For example, when an example is said to "include" a specific feature, that is intended to imply that it may have that feature but not that such examples are limited to those that include that feature.

It must also be noted that, as used in this specification and the appended claims, the singular forms "a," "an," and "the" include plural referents unless the context clearly dictates otherwise. Thus, for example, reference to "a therapeutic agent" includes a single therapeutic agent as well as a combination of two or more therapeutic agents, reference to "a pharmaceutically acceptable carrier" includes a single pharmaceutically acceptable carrier as well as combinations of two or more pharmaceutically acceptable carriers, and the like.

I. Definitions

As used herein, the terms "therapeutic agent" and "drug" are used interchangeably and are intended to include agents that are useful in treating orofacial diseases states and agents that are useful in treating pain and other conditions associated with orofacial disease states. The terms also encompasses pharmaceutically acceptable, pharmacologically active derivatives of those agents specifically mentioned herein, including, but not limited to, salts, esters, amides, prodrugs, active metabolites, analogs, and the like. Such therapeutic agents include by way of illustration and not limitation, anti-inflammatory agents, anti-infective agents, tissue and bone growth factors, pain management medication, antineoplastic agents, bone alteration agents, and combinations thereof. When the term "therapeutic agent" is used, it is also to be understood that the active agent per se as well as pharmaceutically acceptable, pharmacologically active salts, esters, amides, prodrugs, metabolites, analogs, etc. are included.

The term "pharmaceutically acceptable carrier" is intended to mean a material or materials that are suitable for drug administration and not biologically or otherwise undesirable, i.e., that may be administered to an individual along with a therapeutic agent without causing any undesirable biological effects or interacting in a deleterious manner with any of the other components of the pharmaceutical formulation in which it is contained.

The terms "tissue within the orofacial environment" and "orofacial tissue" are used interchangeably to mean tissue sites located within the orofacial environment, which includes the oral cavity, head and neck, including the brain. Such tissue includes by way of illustration and not limitation, periodontal tissue such as the periodontium; periodontal ligaments; bone tissue at the end of an infected tooth, inside the tooth or within the bone cavity such as may be present after an apicoectomy or tooth extraction; endodontic tissue; bone tissue surrounding an implant fixture; ear tissue such as that affected by a stapedectomy procedure; jaw tissue such as the temporomandibular joint, the temporalis muscle, the temporal bone the masseter muscle and the mandible; lymph nodes, glands, like for example thyroid or pituitary, tissue affected by surgery, e.g. tonsillectomy; and so forth.

The terms "intratissue" and "intraorofacial tissue" are used interchangeably and are intended to mean that the controlled release drug delivery system of the invention is positioned inside the orofacial tissue in contrast to topically. The drug delivery system of the invention can be implanted within the tissue by a punch biopsy procedure, inserted into the tissue with a trocar, inserted into the tissue after a surgical incision, left in the open wound after a surgical procedure, and so forth. The term intratissue is intended to include intraosseous. The term specifically excludes supratissue placement such as on top of the gum tissue or intertissue (intersulcular) placement such as within the periodontal pocket.

The term "placement site" is intended to mean the intratissue location of the drug delivery system of the invention. The "target site" is the location of the tissue to be treated. Typically the placement site will be the same as the target site to provide for optimal targeted drug delivery. However, the invention also contemplates positioning the drug delivery system at a placement site nearby the target site such that the therapeutic agent can be delivered to the surrounding vasculature, which carries the agent to the desired nearby target site. As used herein, the term "nearby" implies that the placement site and target site are within close proximity. Preferably, both sites are within the orofacial environment. This drug delivery strategy is of benefit in the case the target site is a larger tissue area or orofacial structure or if it is desired to distribute the agent over a larger tissue segment not only by passive diffusion through the adjacent tissue, but also utilize convective transport via the nearby vasculature. Convective transport is often much faster than passive diffusion and allows for a more effective and far-reaching drug administration. For those skilled in the art the appropriate placement sites can be easily determined by assessing the course of the principal arteries supplying the head and neck that convey oxygenated blood and nutrition to the orofacial tissues. It is known that the two common carotids that ascend in the neck, each divide into two branches, the external carotid, supplying the exterior of the head, the face, and the greater part of the neck and the internal carotid, supplying to a great extent the parts within the cranial and orbital cavities, where they further divide into other branches supplying specific orofacial areas and structures. To those skilled in the art, the specific locations of these artery branches and their anatomical relations to the targeted diseased orofacial tissues are very well known. Distribution of an agent via a blood vessel to a nearby orofacial tissue site (muscle, gland, cavity, nerve, lymph node, teeth, gingiva, eye, ear, joint, brain, etc.) can be selected according to the prevailing nearby blood vessel anatomy and the ability to place the drug delivery system at the desired site. Desired placement sites are easy accessible or locations before the vessel(s) of interest enter(s) a bony cavity or arise(s) from it. Exemplary placement sites that may not also be the target site include the three bilateral sublingual and submandibular glands (open into the floor of mouth, one on each side of the frenulum of the tongue) and the parotid. Their secretions (transferred via long ducts) lubricate the mouth and thus could act to deliver drug from a drug delivery system positioned therein. The advantage with such a placement is that it is quite practical to position a drug delivery system within one of these glands or the parotid, and provide delivery to treat a variety of orofacial diseases. Other glands present in the orofacial environment may also be suitable placement sites, such as the lingual, labial, tonsillar or buccal glands. The strategic placement sites of the drug delivery system may include lymph nodes or the corresponding drainage system. The intercellular spaces contain small endothelial-lined tubes, resembling blood vessels, but are blind ending. The network of these vessels drain the lymph from a particular area into the lymph node serving that area. Primary diseases of the lymphatics that could be treated in this manner includes Hodgkin's disease and lymphatic neoplasms.

The term "orofacial disease" is intended to include, by way of illustration and not limitation, acute and chronic inflammation, including chronic inflammation of the tissue (including host response reactions) to stop the process of the on-going tissue decay; infection; pain and related inflammatory and other complications of mechanical teeth cleaning (including root planning and scaling), all periodontal surgical procedures, and other surgical procedures such as an apicoectomy or root canal, procedures done to facilitate tooth movement such as orthodontia; repair damage to periodontal ligament, bone and other tissues that has been caused by periodontal disease; cranomandibular disease which produces facial, head, ear and jaw pain, examples of which include temporomandibular joint syndrome; ear surgery; eye surgery (including strabismus surgery); drug delivery to the eye (in contrast to intraocular); othoptics; vision therapy; cosmetic and plastic surgery to reconstruct and rebuild facial features after accidents or other deformations; wrinkle removal and anti-wrinkle therapy (e.g. long-lasting Botulinum Toxin Type A delivery); cranial nerve and oculomotor pals; surgical correction of drooping lid; surgery to repair palsies and to prevent amblyopia; meningitis; Parkinson's disease; Alzheimer's disease; brain cancer; viral infections; cold sores; otologic surgery; treatment of Menier's syndrome; ear tumors; otitis and otitis media; otosclerosis; tinnitus; meringotomy; structures of balance; prevention of complications from ear drum perforation; cholesteatomas; sinusitis; mastoditis; tonsillitis; pharyngitis; adenitis; hair transplantation; skin transplants; nose surgery; tonsillectomy; and so forth. The term "orofacial disease" is intended to encompass diseases within the orofacial environment, as well as diseases that originate in the orofacial environment.

The term "treatment" as used herein covers any treatment of any orofacial disease in a mammal, particularly a human, and includes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease. For example, treatment can include reducing acute or chronic inflammation; alleviating pain and mitigating and inducing re-growth of new periodontal ligament, bone and other tissues; as an adjunct in orthognathic surgery; any elective cosmetic surgical or repair procedure; and so forth.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art. Typically, the drug delivery system of the invention administers the therapeutic agent at a predefined and controlled release rate that creates local concentration levels within the desired therapeutic range or therapeutic index of the drug. The upper limit of this therapeutic range prevents toxicity and other unwanted effects, while the lower limit of the range prevents sub-therapeutic levels from being administered.

The invention pertains to methods and drug delivery systems for the treatment of a variety of diseases within or originating in the orofacial environment. These methods generally involve the step of administering a controlled release drug delivery system inside the diseased tissue. The controlled release drug delivery systems useful in these methods generally comprise a depot and at least one therapeutic agent encapsulated, dissolved or dispersed therein, and are described in detail below. In general, the therapeutic agent can be any therapeutic that is useful in treating diseases within or originating in the orofacial environment. Specific non-limiting examples are set forth below.

One embodiment of the invention is a drug delivery system configured to be positioned within orofacial tissue comprising a semi-solid or solid depot and at least one therapeutic agent contained therein, and having a size within the range of about 0.03–17 cubic millimeters ($mm^3$). The actual size selected will be based upon considerations such as the average daily dosage, the drug loading capacity and duration of delivery, drug delivery density, and so forth.

The following table exemplifies numerous variables (all stated as approximations) that affect the size selected for the drug delivery system.

| desired average daily dosage (μg/day) | drug loading (wt %) | density (g/cm³) | duration | size (mm³) |
|---|---|---|---|---|
| 5–10 | 30–90 | 0.9–1.3 | 7–14 days | 0.03–0.5 |
| 5–10 | 30–90 | 0.9–1.3 | up to 1 month | 0.13–1.1 |
| 5–10 | 30–90 | 0.9–1.3 | 2 months | 0.26–2.2 |
| 5–10 | 30–90 | 0.9–1.3 | 3 months | 0.38–3.3 |
| 25–50 | 30–90 | 0.9–1.3 | up to 2 weeks | 0.15–2.6 |
| 25–50 | 30–90 | 0.9–1.3 | up to 1 month | 0.64–5.6 |
| 25–50 | 30–90 | 0.9–1.3 | 2 months | 1.3–11 |
| 25–50 | 30–90 | 0.9–1.3 | 3 months | 1.9–17 |

These are only intended to be exemplary in nature. The final drug delivery system size will vary as the above-mentioned parameters are varied within and beyond the exemplary ranges. Since small drug delivery systems sizes are preferred, active agents with high potency that require low concentration levels are desired for the incorporation into the drug delivery system. To further minimize the size, drug delivery system designs that allow for a high agent loading are preferred that also have an overall high density. Therapies with shorter drug delivery requirements will require smaller drug delivery sizes as compared to therapies that require long-term delivery.

The size of the drug delivery systems of the invention can also be approximated by using the following mathematical equation:

$$\text{Drug delivery system size (mm}^3\text{)} = \frac{\text{Average Daily dose (μg/day)} \times \text{duration (days)}}{\text{Load \%} \times \text{density (g/cm}^3\text{)} \times 10}$$

Another embodiment of the invention is a drug delivery system configured to be positioned within orofacial tissue comprising a semi-solid or solid depot and about 35–4500 μg of a therapeutic agent contained therein, depending on the daily dosage requirement and the desired length of the therapeutic delivery and having a corresponding size within the range of about 0.03–17 mm³.

Specific details regarding the composition and configuration of these systems are set forth below.

II. The System

The controlled release drug delivery system is typically comprised of an agent-containing depot and is packaged in a manner suitable for successful long-term storage. The depot acts as the source of or carrier for the therapeutic agent, and can take any of the forms commonly known in the art, such as a reservoir system including capsules and other encapsulated formulations; monolith systems including monolith solutions and monolith dispersions; sponges; and so forth. The drug delivery system may be comprised solely of the agent-containing depot, or may optionally include additional functional features such as a membrane, a backing layer, an adhesive layer, a release liner, and so forth. Such features are well known to those skilled in the art and thus will only be briefly described below.

A reservoir is typically an inert membrane enclosing the agent-containing core. The agent diffuses through the thin rate-controlling membrane at a finite, controllable rate. One example is an encapsulated formulation or capsule, which is comprised of an internal core of therapeutic agent, e.g., in a liquid form, encapsulated by a drug-permeable membrane.

A monolith can be of solution or dispersion-type, both of which are homogeneous mixtures of the depot material and the therapeutic agent, i.e., the therapeutic agent is dispersed uniformly throughout a rate-controlling material that forms the depot. In general, monoliths systems may have additional layers such as a drug-permeable membrane, adhesive layer and so forth, and may therefore constitute a mixed reservoir/monolithic system.

Monolithic dispersions include simple monoliths, complex monoliths and matrix monoliths, all of which are all suitable for use as drug delivery systems of the invention. A simple monolith is a drug depot formed of a suitable material having the drug dispersed within the material, where $Cs<Co<5\%$. For a complex monolith, $5\%<Co<15\%$. In both cases drug particles are dispersed at low concentrations throughout the depot forming material. The concentration is low enough to prevent substantial interconnection of dispersed drug particles, i.e. each drug particle is essentially surrounded by depot forming material. On its way to the target disease site, a drug molecule has to dissolve from the dispersed drug particle and partition into the depot forming material of the drug delivery system. Here it diffuses according to its thermodynamic driving force to the outside of the drug delivery system, where it now has to partition into the drug delivery system surrounding environment. For a matrix monolith the loading concentration is substantially higher, typically $Co>15\%$. In that case (matrix system), according to the percolation theory, the dispersed drug particles can now connect to each other and drug delivery may be governed by additional drug diffusion through the developing pores. In this case the outermost drug particles on the depot's surface are dissolving first, creating an opening to the underlying next dispersed drug particle. This particle is now dissolving opening space for the next underlying dispersed drug particles. Often the diffusion through the establishing pores that are filling with the drug delivery system surrounding fluid, is faster than through the depot forming material.

In general monoliths systems may have additional layers such as a drug-permeable membrane, adhesive layer and so forth, and may therefore constitute a mixed reservoir/monolithic system.

The controlled release drug delivery system can also be configured as a sponge or microporous structure, which would be loaded with drug by soaking or absorption into the microporous structure. This configuration is particularly useful when the system is to be used in conjunction with a tooth extraction or other procedure where a large hole has been created due to surgery or disease. In this manner, the drug delivery system would provide structural benefits, as well as function to deliver the therapeutic agent.

Each depot type has its advantages. Monolithic dispersions are relatively easy to manufacture, while encapsulated formulations can provide greater control of the drug release profile. Selection of the depot material itself will take into consideration factors such as compatibility of the material with the therapeutic agent, ease of manufacturing, the desired therapeutic delivery profile, and so forth. Of particular interest is also, the ability to administer drug delivery systems that do not require potentially harmful processing solvents or contain inactive ingredients that may have toxicological functions. The drug delivery systems of the invention minimize or eliminate the need for such ingredients, including solvents, etc.

There are various methods that are well known in the art by which the monolith, encapsulated formulation, sponge, and so forth can be manufactured. Such methods include, solvent evaporation methods, phase separation methods, interfacial methods, extrusion methods, molding methods, injection molding methods, heat press methods, and so forth.

Typically, the system will be designed to release the therapeutic agent over a period of at least about 3 days, typically at least about 7 days. While typical regimens will not last longer than about 31 days, the systems can be designed to release the therapeutic agent over a period of up to 90 days. In one embodiment, the system is designed to release the therapeutic agent for about 3–7 days. In another embodiment, the system is designed to release the therapeutic agent for about 14–30 days. In still another embodiment, the system is designed to release the therapeutic agent for about 30–90 days. Such systems will be able to deliver therapeutic agents to a targeted site in the orofacial environment at a rate of about 5–50 µg per day for the aforementioned therapeutic time frames. Preferably about 5–35 µg per day, more preferably about 7–15 µg per day of therapeutic agent will be administered. The delivery system size for the most preferred case will be within the range of about 0.1 to 3 $mm^3$, for delivery intervals ranging from 1-week to 3-months having a drug load of about 50%.

It is expected that the release profile and duration will vary with the disease state that is being treated. Exemplary disease states are described in detail below.

A. The Depot

The depot contains the active agent or agents and may also contain other non-active ingredients. It has a multi-functional purpose including the carrying, stabilizing and controlling the release of the active agent(s). The controlled release process, for example, may be by a solution-diffusion mechanism or it may be governed by an erosion-controlled process. The depot will typically be a solid or semi-solid formulation comprised of a biocompatible material, which can be biodegradable or non-biodegradable. The term "solid" is intended to mean a rigid material, while, "semi-solid" is intended to mean a material that has some degree of flexibility, thereby allowing the drug delivery system to bend and conform to the surrounding tissue requirements.

The depot material, as well as any other components of the system will preferably be durable within the tissue site for a period of time equal to (for biodegradable components) or greater than (nor non-biodegradable components) the planned period of drug delivery. For example, the depot material may have a melting point or glass transition temperature close to or higher than body temperature, but lower then the decomposition or degradation temperature of the therapeutic agent. However, the pre-determined erosion of the depot material can also be used to provide for slow release of the loaded agent(s).

The depot preferably has a high drug loading, such that the therapeutic agent comprises about 5–99 wt % of the depot, preferably 30–95 wt % of the depot, and more preferably 50–95 wt % of the depot. The balance is depot material, including optional inactive materials. While the actual amounts of the depot materials can vary within acceptable parameters, it is preferred to minimize the total amount of depot materials so as to maximize the overall drug carrying capability of the drug delivery system and therefore minimizing the overall drug delivery system size.

1. Materials a. Biodegradable Materials

In some instance, it may be desirable to avoid having to remove the controlled release drug delivery system after use. In those instances, the depot is preferably comprised of a biodegradable material. There are numerous materials available for this purpose and having the characteristic of being able to break down or disintegrate over a prolonged period of time when positioned within the target tissue. As function of the chemistry of the biodegradable material the mechanism of the degradation process can be hydrolytical or enzymatical in nature, or both. The degradation preferably occurs either at the surface (heterogeneous or surface erosion) or uniformly throughout the drug delivery system depot (homogeneous or bulk erosion).

Typically, to form biodegradable polymers labile bonds are introduced in the polymer. Those labile bonds may be in the polymer backbone, so that cleavage creates low-molecular, water-soluble polymer fragments. The unstable bonds could also be part of a pendent side chain where the labile bond attaches an often hydrophobic side group to a water-soluble polymer. Furthermore, the unstable bonds could be part of a cross-linked network and upon cleavage in the cross-links producing soluble fragments.

Suitable materials are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

Suitable biodegradable polymeric materials include, by way of illustration and not limitation, the widely studied esters of poly(glycolic acid) and poly(lactic acid) and their copolymers where the degradation rate is controlled by the ratio of glycolic acid to lactic acid, as well as copolyoxalates, polycaprolactone, poly(lactide-co-caprolactone), poly(esteramides), polyorthoesters, polyanhydrides, polyacrylic acid, etc.

Other suitable biodegradable materials include collagens; gelatin and pre-gelatinized starch; hyaluronic acid; polysaccharides such as calcium alginate; proteins such as albumin and fibrin; and combinations thereof. Numerous other biodegradable polymeric materials are well known to those of skill in the art and therefore the aforementioned list is not intended to limit the invention in any manner.

Suitable biodegradable non-polymeric materials include, by way of illustration and not limitation, natural and synthetic materials such as Vitamin E analogs such as the esters d-α-tocopheryl acetate and d-α-tocopheryl succinate. Numerous other biodegradable non-polymeric materials that can utilized to form the drug delivery depot are well known to those of skill in the art and therefore the aforementioned list is not intended to limit the invention in any manner.

Vitamin E esters such as d-α-tocopheryl acetate and d-α-tocopheryl succinate are particularly well suited for use as a biodegradable non-polymeric depot material. These esters are solids at body temperature but have relatively low melt points (28° C. and 76° C., respectively). Therefore, the drug delivery system can be easily manufactured by melting the Vitamin E ester at a low temperature and the therapeutic agent can be admixed into the melt. The melt is then readily sub-divided into dosage units and cooled until solidified. Use of Vitamin E esters as the depot materials also provides additional benefits since the esters can also serve to stabilize instable therapeutic agents, as well as function as permeation enhancers to increase tissue absorption of the therapeutic agent.

b. Non-Biodegradable Materials

In some instance, it may be acceptable to remove the controlled release drug delivery system after use, such as when a surgical procedure is expected to follow placement of the system. In those instances, the drug delivery system depot can be comprised of a non-biodegradable material. There are numerous such materials that can be used for the agent-containing depot in the drug delivery system of the invention. These non-biodegradable materials can be polymeric or non-polymeric, as well as synthetic or naturally occurring, or a combination thereof. However, the material will typically be a synthetic polymer, and can be a homopolymer or copolymer, straight or branched, and can have varying degrees of cross-linking.

These include, by way of illustration and not limitation, cellulose derived polymers such as ethylcellulose, hydroxyethyl cellulose, hydroxypropylcellulose, hydroxypropylmethylcellulose and methylcellulose, as well as functionalized celluloses such as calcium carboxymethylcellulose, carboxymethylcellulose esters and sodium carboxymethylcellulose; poly(vinyl acetate) and so forth; chlorinated poly(ethylene); cross-linked poly(vinylpyrrolidone); ethylene-propylene rubber; ethylene-vinyl ester copolymers such as ethylene-vinyl acetate copolymer, ethylene-vinyl hexanoate copolymer, ethylene-vinyl propionate copolymer, ethylene-vinyl butyrate copolymer, ethylene-vinyl pentanoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer and ethylene-vinyl benzoate copolymer; natural rubber; plasticized poly(amides); plasticized nylon; plasticized poly(ethylene terephthalate); plasticized poly(vinylchloride); poly(acrylate); poly(acrylonitrile); poly(alkylmethacrylates) such as poly(methylmethacrylate) and poly(butylmethacrylate); poly(amides); poly(butadiene); polycarbamates or polyureas such as polyurethane polymers; poly(carbonates); poly(dimethylsiloxanes); poly(esters); poly(ethylene); poly(halo-olefins); poly(isobutylene); poly(isoprene); poly(4,4'-isopropylidene diphenylene carbonate); poly(styrene); poly(tetrafluoroethylene); poly(trifluorochloroethylene); poly(methacrylate); poly(olefins); poly(oxides); poly(vinyls); poly(vinylidene chloride); and poly(vinyl-olefins); silicone; silicone-carbonate copolymers; silicone rubbers, particular medical grade; vinyl chloride-acrylonitrile copolymers; vinylidene chloride-acrylonitrile copolymers; vinyl chloride diethyl fumarate copolymers; and vinylidene chloride-vinyl chloride copolymers. Numerous other non-biodegradable polymeric materials are well known to those of skill in the art and therefore the aforementioned list is not intended to limit the invention in any manner.

Suitable non-biodegradable non-polymeric materials include, by way of illustration and not limitation, all those materials used in the field of dentistry such as restorative materials (e.g., amalgams, composites, glass ionomers), bases, cements, liners, adhesives, impression materials, gypsum products, acrylics, and so forth. Numerous other non-biodegradable non-polymeric materials are well known to those of skill in the art and therefore the aforementioned list is not intended to limit the invention in any manner.

Since the rate of release of the therapeutic agent from a non-biodegradable material will mainly be by diffusion, selection of suitable materials should take into consideration factors such as the solubility of the therapeutic agent, the hydrophilic characteristics of the material, the amount of cross-linking (for polymeric materials), the amount of swelling that the material may undergo upon absorption of water, and so forth.

It may also be acceptable to leave the system in place after drug delivery is complete, so as to further serve as "scaffolding" for the regrowth of tissue. In this instance, the drug delivery system depot can also be formulated from a non-biodegradable particle former, e.g. compounds that are used already in the dental arena which include gutta perch, or the typical scaffolding materials, and so forth.

2. Therapeutic Agents

The methods and controlled release drug delivery systems of the invention find utility in administering therapeutic agents to treat numerous orofacial diseases states, including treating pain and other conditions associated with orofacial disease states. The methods and systems of the invention can be used with any therapeutic that is useful in treating diseases within or originating in the orofacial environment. Examples of such agents include by way of illustration and not limitation, anti-inflammatory agents, anti-infective agents, tissue and bone growth factors, pain management medication, antineoplastic agents, bone alteration agents, and combinations thereof. The therapeutic agent can also be a thyroid drug, i.e., anti-thyroid agents or thyrostatic substances that are compounds useful for the treatment of thyroid diseases, including hormones such as thyroxine (T4), triiodothyronine (T3); propylthiouracil; methimazole; and so forth.

A single drug delivery system contains at least one therapeutic agent, and thus may contain one or more additional therapeutic agents. However, in another embodiment of the invention, combination therapy will involve use of single agent systems. For example the method may further comprise subsequently administering one or more additional drug delivery systems, each containing a therapeutic agent that is different from the therapeutic agent contained in the first drug delivery system. This provides for a "mix and match" therapeutic regimen with dose adjustment capability. Due to the small size of the controlled release drug delivery systems of the invention, a plurality of systems (each containing a different therapeutic agent) can readily be intratissually positioned at the target site and/or several drug delivery systems containing the same agent can be administered. This provides the added advantage of allowing the physician complete control to administer only those agents at the desired strength believed to be appropriate for the disease state being treated.

The amount of therapeutic agent contained within the controlled release drug delivery systems of the invention, will vary widely depending on the effective dosage required and rate of release from the system and the length of the desired delivery interval. Typically, the therapeutic agent will be present in microgram quantities, typically within the range of about 35–1500 µg, preferably about 50–750 µg, more preferably about 50–450 µg for drug delivery intervals of up to 1 month. For drug delivery intervals of up to 3 months the therapeutic agent will be present typically within the range of about 450–4500 µg, preferably about 210–2250 µg, more preferably about 210–1350 µg.

a. Anti-inflammatory Agents

Anti-inflammatory agents are of particular interest as it is believed that they serve not only to reduce inflammation but, in doing so, can also have a variety of other beneficial effects that may eliminate the need for or minimize the amount of additional therapeutic agents. For example, if a patient is suffering from pain and inflammation, administration of an anti-inflammatory agent will alleviate inflammation and the tissue, once back to normal may no loner exert pressure on nerves and thus the need to additional pain medication may be minimized or eliminated entirely.

Suitable anti-inflammatory agents to treat and reduce inflammation include both steroidal and non-steroidal anti-inflammatories. Exemplary anti-inflammatory agents include by way of example and not limitation, alclofenac; alclometasone dipropionate; algestone acetonide; alendronate sodium; alpha amylase; amcinafal; amcinafide; amcinonide; amfenac sodium; amiprilose hydrochloride; anakinra; anirolac; anitrazafen; apazone; balsalazide disodium; beclomethasone dipropionate; bendazac; benoxaprofen; benzydamine hydrochloride; betamethasone; bromelains; broperamole; budesonide; carprofen; cicloprofen; cintazone; cliprofen; clobetasol propionate; clobetasone butyrate; clopirac; cloticasone propionate; cormethasone acetate; cortisone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; fludrocortisone; flufenamic acid; flumizole; flunisolide acetate; flunixin; flunixin meglumine; fluocinonide; fluocinolone acetonide; fluocortin butyl; fluoromethalone acetate; fluquazone; flurandrenolide; flurbiprofen; fluretofen; fluticasone propionate; furaprofen; furobufen; halcinonide; halobetasol propionate; halopredone acetate; hydrocortisone; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisone dibutyrate; medrysone; mefenamic acid; mesalamine; meseclazone; methylprednisolone suleptanate; momiflumate; nabumetone; naproxen; naproxen sodium; naproxol; nimazone; nilutamide; olsalazine sodium; orgotein; orpanoxin; oxaprozin; oxyphenbutazone; pamidronate disodium; paramethasone; paranyline hydrochloride; pentosan polysulfate sodium; phenbutazone sodium glycerate; pirfenidone; piroxicam; piroxicam cinnamate; piroxicam olamine; pirprofen; prednazate; prednisolone; prifelone; prodolic acid; proquazone; proxazole; proxazole citrate; rimexolone; romazarit; salcolex; salnacedin; salsalate; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triamcinelone; triclonide; triflumidate; zidometacin; zomepirac sodium; and combinations thereof.

A preferred class of anti-inflammatory agents are the steroidal agents or glucocorticosteroids. Phospholipase A2 ("PLA2") is a lipolytic enzyme that has been implicated as a possible mediator of inflammation. Specifically, PLA2 hydrolyses the 2-acyl position of glycerophospholipids, liberating free-fatty acids, mainly arachidonic acid. Subsequently, it is believed that arachidonic acid is converted into a variety of proinflammatory eicosanoids. Glucocorticosteroids are known to stop or reduce the suggested mechanisms of inflammation that involves the activation of the arachidonic acid cascade which results in the liberation of a variety of proinflammatory eicosanoids by inducing lipocortin that inhibits PLA2. This provides a significant advantage over non-steroidal anti-inflammatory agents that enter the cascade much later.

Suitable glucocorticosteroids include agents such as alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluoromethalone acetate, flurandrenolide, halcinonide, medrysone, methylprednisone suleptanate, pamidronate, paramethasone, prednisolone, nilutamide, triamcinelone, and combinations thereof.

Dexamethasone is of particular interest for use as an anti-inflammatory to treat orofacial diseases. Besides its anti-inflammatory property, dexamethasone can be delivered to up-regulate certain enzyme activities. Specifically dexamethasone can be used to increase or up-regulate alkaline phosphotase activity in regenerating human periodontal cells, as described by Kuru et al., *J. Periodont Res.* 34:123–127 (1999).

b. Anti-infective Agents

Exemplary anti-infective agents to treat infection include by way of example and not limitation, antibacterial agents; quinolones and in particular fluoroquinolones (e.g. norfloxacin, ciprofloxacin, lomefloxacin, ofloxacin, etc.); and other broad spectrum antibiotics having a low minimum inhibitory concentrations ("MIC") or low bactericidal concentrations ("MBC") including aminoglycosides (e.g. gentamycin, tobramycin, etc.), glycopeptides (e.g. vancomycin, etc.), lincosamides (e.g. clindamycin), cephalosporins and related beta-lactams (preferably third generation), macrolides (e.g. azithromycin, erythromycin, etc.), nitroimidazoles (e.g. metronidazole), penicillins, polymyxins, tetracyclines, and combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; and combinations thereof.

Of particular interest are those anti-infective agents that have low minimum inhibitory or bactericidal concentrations ("MIC" or "MBC") such as quinolones in particular fluoroquinolones, and so forth, as noted above. Typically such MIC or MBC values will be less than about 5 µg/ml. There are several methods to evaluate an organism's (e.g., bacteria) level of resistance to an anti-infective agent. Typically, serial dilutions of the agent are made in a liquid medium which is inoculated with a standardized number of organisms and incubated for a prescribed time. The lowest concentration (highest dilution) of agent preventing appearance of turbidity is considered to be the "minimum inhibitory concentration". At this dilution the agent is considered to be bacteriostatic.

The systems of this invention are particularly well suited for the administration of low "MIC" anti-infective agents due to the small size of the system. For example a high MIC drug requires a similarly high dosage to be effective, and thus would require a large drug delivery system to accommodate the needed dosage amount. A low MIC drug that is 1000 times more potent than the high MIC drug, would require 1000 time less drug, and therefore a suitable drug delivery system could similarly be 1000 times smaller.

Typically, orofacial infections are polymirobial and dominant organisms can vary greatly. The most common organisms found in periodontal disease include *Spirochete, Streptococcus mutans, Streptococcus oralis, Streptococcus sanguis, Actinomyces naeslundi, Porphyromonas gingivalis, Prevotella intermedia, Fusobacterium nucleatum, Peptostreptococcus micros, Actinmyces naeslundi, Leptotrichia buccalis, Eikenella corrodens, Microaerophillic streptococci*, and so forth. Exemplary anti-infective agents with low MICs that can be used in the methods of the invention include aminoglycosides such as gentamycin and tobramycin; dicloxacillin; fluoroquinolones such as ciprofloxacin; glycopeptides such as vancomycin; lincosamides such as clindamycin; macrolides such as azithromycin and erythromycin; nitroimidazoles such as metronidazole; oxacillin; penicillins; tetracyclines; and so forth.

c. Tissue and Bone Growth Factors

Exemplary tissue and bone growth factors to facilitate tissue and/or bone growth include by way of example and not limitation, growth hormones such as transforming growth factor-β. There are also other factors or enzymes such as alkaline phosphatase that are involved in the facilitation of tissue and/or bone regeneration. Alkaline phosphatase has been shown to be a biochemical indicator of bone turnover. Osteoblasts, generally regarded as bone forming cells, arise from marrow stroma cells. They are found on the surfaces where bone is being formed. Their most obvious function is to synthesize osteoid and collagen and control its subsequent mineralization. Both cytoplasm and nucleus of osteoblasts contain the enzyme alkaline phosphatase, which can be used as a marker for osteoblast activity. Alkaline phosphatase is a calcium- and phosphate binding protein that is distributed for example in periodontal ligament and more prominent in regions close to the alveolar bone and markedly lower in gingival connective tissue. Drugs, like dexamethasone, promote the differentiation of osteoprogenitor cells into osteoblasts and therefore can be used in lieu of growth factors.

Tissue and bone growth factors can also be administered to reduce tissue destruction and/or bone loss, such as to reduce alveolar bone loss. Such tissue and bone growth factors are referred to herein as anti-degenerative agents and include by way of example and not limitation, cyclooxygenase inhibitors such as 2',4,4'-tricholoro-2-hydroxydiphenylether; non-antimicrobial tetracyclines such as 12α-deoxytetracyclines; matrix metalloendoproteinase inhibitors such as inhibitors of collagenase, stormelysin and gelatinase; 5-lipoxygenase inhibitors such as quinolones; nonsteroidal anti-inflammatory drugs such as etodolac; bisphosphonates such as alendronate and etidronate; and combinations thereof.

Of particular interest are NSAIDs such as etodolac, which exhibits anti-inflammatory, analgesic, and antipyretic activities. The mechanism of action of etodolac, like that of other NSAIDs, is not known, but is believed to be associated with the inhibition of prostaglandin biosynthesis. Bisphosphonates are also of particular interest, for example, alendronate sodium, which is an aminobisphosphonate that acts as a specific inhibitor of osteoclast-mediated bone resorption. Bisphosphonates are synthetic analogs of pyrophosphate that bind to the hydroxyapatite found in bone. At the cellular level, alendronate shows preferential localization to sites of bone resorption, specifically under osteoclasts. Alendronate does not interfere with osteoclast recruitment or attachment, but it does inhibit osteoclast activity. Studies in mice on the localization of radioactive [$^3$H]alendronate in bone showed about 10-fold higher uptake on osteoclast surfaces than on osteoblast surfaces. After alendronate administration normal bone is formed on top of the alendronate, which is incorporated inside the matrix. While incorporated in bone matrix, alendronate is not pharmacologically active. Thus, alendronate is preferably continuously administered to suppress osteoclasts on newly formed resorption surfaces. In alendronate treatment bone formation exceeds bone resorption at these remodeling sites, leading to progressive gains in bone mass.

Drugs like phenytoin (dilantin) can also be delivered to facilitate gum tissue re-growth. Phenytoin is an antiepileptic drug and is related to the barbiturates in chemical structure. Typically, it is administered to treat seizures and epilepsy. One of its pharmaceutical side-effects (gingival hyperplasia) can be used to enhance the gingival tissue regeneration.

d. Pain Management Medication

The term "pain management medication" covers an assortment of therapeutic agents that are administered to prevent, alleviate or remove pain entirely. These include anti-inflammatory agents, muscle relaxants, analgesics, anesthetics, narcotics, and so forth, and combinations thereof.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, and combinations thereof.

Of particular interest is chlorphenesin carbamate, a drug which also has antifungal activity. Chlorphenesin carbamate is used in the treatment of trigeminal neuralgia, a disorder of the fifth cranial (trigeminal) nerve that causes episodes of intense, stabbing, electric shock-like pain in the areas of the face where the branches of the nerve are distributed, such as the lips, eyes, nose, scalp, forehead, upper jaw, and lower jaw. Simples and routine acts such as brushing the teeth, putting on makeup or even a slight breeze can trigger an attack, resulting in sheer agony for the individual. Trigeminal neuralgia ("TN") is not fatal, but it is universally considered to be the most painful affliction known to medical practice. Initial conventional treatment of TN is usually by means of anti-convulsant or antiepileptic drugs, such as carbamazepine or gabapentin. Some anti-depressant drugs also have significant pain relieving effects Exemplary analgesics include by way of example and not limitation, acetaminophen; alfentanil hydrochloride; aminobenzoate potassium; aminobenzoate sodium; anidoxime; anileridine; anileridine hydrochloride; anilopam hydrochloride; anirolac; antipyrine; aspirin; benoxaprofen; benzydamine hydrochloride; bicifadine hydrochloride; brifentanil hydrochloride; bromadoline maleate; bromfenac sodium; buprenorphine hydrochloride; butacetin; butixirate; butorphanol; butorphanol tartrate; carbamazepine; carbaspirin calcium; carbiphene hydrochloride; carfentanil citrate; ciprefadol succinate; ciramadol; ciramadol hydrochloride; clonixeril; clonixin; codeine; codeine phosphate; codeine sulfate; conorphone hydrochloride; cyclazocine; dexoxadrol hydrochloride; dexpemedolac; dezocine; diflunisal; dihydrocodeine bitartrate; dimefadane; dipyrone; doxpicomine hydrochloride; drinidene; enadoline hydrochloride; epirizole; ergotamine tartrate; ethoxazene hydrochloride; etofenamate; eugenol; fenoprofen; fenoprofen calcium; fentanyl citrate; floctafenine; flufenisal; flunixin; flunixin meglumine; flupirtine maleate; fluproquazone; fluradoline hydrochloride; flurbiprofen; hydromorphone hydrochloride; ibufenac; indoprofen; ketazocine; ketorfanol; ketorolac and ketorolac tromethamine; letimide hydrochloride; levomethadyl acetate; levomethadyl acetate hydrochloride; levonantradol hydrochloride; levorphanol tartrate; lofemizole hydrochloride; lofentanil oxalate; lorcinadol; lomoxicam; magnesium salicylate; mefenamic acid; menabitan hydrochloride; meperidine hydrochloride; meptazinol hydrochloride; methadone hydrochloride; methadyl acetate; methopholine; methotrimeprazine; metkephamid acetate; mimbane hydrochloride; mirfentanil hydrochloride; molinazone; morphine sulfate; moxazocine; nabitan hydrochloride; nalbuphine hydrochloride; nalmexone hydrochloride; namoxyrate; nantradol hydrochloride; naproxen; naproxen sodium; naproxol; nefopam hydrochloride; nexeridine hydrochloride; noracymethadol hydrochloride; ocfentanil hydrochloride; octazamide; olvanil; oxetorone fumarate; oxycodone; oxycodone hydrochloride; oxycodone terephthalate; oxymorphone hydrochloride; pemedolac; pentamorphone; pentazocine; pentazocine hydrochloride; pentazocine lactate; phenazopyridine hydrochloride; phenyramidol hydrochloride; picenadol hydrochloride; pinadoline; pirfenidone; piroxicam olamine; pravadoline maleate; prodilidine hydrochloride; profadol hydrochloride; propirarn fumarate; propoxyphene hydrochloride; propoxyphene napsylate; proxazole; proxazole citrate; proxorphan tartrate; pyrroliphene hydrochloride; remifentanil hydrochloride; salcolex; salethamide maleate; salicylamide; salicylate meglumine; salsalate; sodium salicylate; spiradoline mesylate; sufentanil; sufentanil citrate; talmetacin; talniflumate; talosalate; tazadolene succinate; tebufelone; tetrydamine; tifurac sodium; tilidine hydrochloride; tiopinac; tonazocine mesylate; tramadol hydrochloride; trefentanil hydrochloride; trolamine; veradoline hydrochloride; verilopam hydrochloride; volazocine; xorphanol mesylate; xylazine hydrochloride; zenazocine mesylate; zomepirac sodium; zucapsaicin; and combinations thereof.

Exemplary anesthetics include by way of example and not limitation, aliflurane; benoxinate hydrochloride; benzocaine; biphenamine hydrochloride; bupivacaine hydrochloride; butamben; butamben picrate; chloroprocaine hydrochloride; cocaine; cocaine hydrochloride; cyclopropane; desflurane; dexivacaine; diamocaine cyclamate; dibucaine; dibucaine hydrochloride; dyclonine hydrochloride; enflurane; ether; ethyl chloride; etidocaine; etoxadrol hydrochloride; euprocin hydrochloride; fluroxene; halothane; isobutamben; isoflurane; ketamine hydrochloride; levoxadrol hydrochloride; lidocaine; lidocaine hydrochloride; mepivacaine hydrochloride; methohexital sodium; methoxyflurane; midazolam hydrochloride; midazolam maleate; minaxolone; nitrous oxide; norflurane; octodrine; oxethazaine; phencyclidine hydrochloride; pramoxine hydrochloride; prilocaine hydrochloride; procaine hydrochloride; propanidid; proparacaine hydrochloride; propofol; propoxycaine hydrochloride; pyrrocaine; risocaine; rodocaine; roflurane; salicyl alcohol; sevoflurane; teflurane; tetracaine; tetracaine hydrochloride; thiamylal; thiamylal sodium; thiopental sodium; tiletamine hydrochloride; zolamine hydrochloride; and combinations thereof.

e. Antineoplastic Agents

Exemplary antineoplastic agents include by way of example and not limitation, acivicin; aclarubicin; acodazole hydrochloride; acrqnine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; ethiodized oil I 131; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; gold Au 198; hydroxyurea; idarubicin hydrochloride; ifosfamide; ilmofosine; interferon α-2a; interferonα-2b; interferon α-n1; interferon α-n3; interferon β-Ia; interferon γ-Ib; iproplatin; irinotecan hydrochloride; lanreotide acetate; letrozole; leucovorin in combination with fluorouracil or methotrexate; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safmgol; safingol hydrochloride; semustine; simtrazene; sparfosate sodium; sparsomycin; spirogermanium hydrochloride; spiromustine; spiroplatin; streptonigrin; streptozocin; strontium chloride Sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; and combinations thereof.

For the treatment of cancers of the head and neck, including cancers of the oral cavity, oropharyngeal cancer, cancer of the nose, cancer in the bones of the face, cancer of the ear, cancer of the eye, skin of the eyelids, cancer of the lymph nodes, cancer of the thyroid gland, larynx and salivary glands, paranasal sinuses, the nasopharynx and ocular melanoma, preferred antineoplastic agents include, by way of illustration and not limitation, carboplatin, cisplatin, cyclophosphamide, fluorouracil, leucovorin in combination with fluorouracil, leucovorin in combination with methotrexate, methotrexate, and combinations thereof.

f. Bone Alteration Agents

Exemplary bone alteration agents to facilitate bone movement include by way of example and not limitation, eicosanoids. This class of compounds includes the prostaglandin, thromboxane and leukotriene families. The eicosanoid class of compounds also includes the common precursor, arachidonic acid and compounds such as alfaprostol, alprostadil, arbaprostil,methyl, carboprost, ciprostene, cloprostenol sodium, dinoprost, dinoprostone, enaprostil, epoprostenol, fenprostalene, fluprostenol sodium, iloprost, gemeprost, luprostiol, meteneprost, misoprotol, prostalene, rosaprostol, sulprostone, trimoprostil, viprostol; and combinations thereof.

3. Optional Ingredients

The depot may optionally contain inactive materials such as buffering agents and pH adjusting agents such as potassium bicarbonate, potassium carbonate and potassium hydroxide, sodium acetate, sodium borate, sodium bicarbonate, sodium carbonate and sodium hydroxide and sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; cohesion modifiers, typically high molecular weight compounds as described above, that may be branched and where the short side-chains could in addition potentially provide or facilitate adherence of the drug delivery system to the orofacial tissue; and so forth. Typically, any such inactive materials will be present within the range of 0–75 wt %, and more typically within the range of 0–30 wt %.

B. Configuration

There are several factors that can be taken into consideration in determining the size, shape and configuration of the drug delivery system. For example, both the size and shape preferably allow for ease in positioning the system inside the region of the diseased oral tissue that is selected as the implantation or injection site. In addition, the shape and size of the system should be selected so as to minimize or prevent the system from moving after implantation or injection.

The system can be shaped like a sphere, a cylinder such as a rod or fiber, a flat surface such as a disc, film or sheet, and so forth. Flexibility may be a consideration so as to facilitate placement of the system in the diseased oral tissue.

The size of the drug delivery system is critical for the treatment efficacy and the general patient's acceptance. Often local dimensions associated with the specific treatment or therapies restrict the drug delivery system size. Therefore, the drug delivery system of the invention preferably has very small dimensions. Typically the higher the amount of loaded therapeutic agent(s) per total delivery system amount, the smaller is the drug delivery system at a given dose or at a given drug delivery system weight the higher the loaded total dose. Consequently, by maximizing the loaded therapeutic agent(s) amount(s), either the drug delivery interval can be extended or the local drug concentration can elevated at a given drug delivery system size. Therefore, one of the unique features of this invention is the potential for designing a very small drug delivery system. This results in the ability to position the system within the target tissue so as to optimize drug delivery to the targeted region that cannot be achieved with current products. In doing so, minute amounts of otherwise toxic drugs can be administered at maximum effect. In this manner, depending on the average daily dosage, drug loading capacity and duration of delivery and drug delivery density, the volume of the drug delivery system will typically be within the range of about 0.03–17 cubic millimeters ($mm^3$) in size. The following table exemplifies several variables (all stated as approximations) that affect the size selected for the drug delivery system.

| desired average daily dosage (μg/day) | drug loading (wt %) | density (g/cm³) | duration | size (mm³) |
|---|---|---|---|---|
| 10–25 | 50–70 | 1 | up to 2 weeks | 0.28–0.7 |
| 10–25 | 50–70 | 1 | up to 1 month | 0.6–1.5 |
| 10–25 | 50–70 | 1 | 2 month | 1.2–3 |
| 10–25 | 50–70 | 1 | 3 months | 1.8–4.5 |

Approximate dimensions of exemplary drug delivery systems of the invention are as follows:

| Configuration | Dimension Range | Exemplary 1 week system[a] | Exemplary 4 week system[b] |
|---|---|---|---|
| Spherical | | | |
| Diameter | about 50 μm to 3 mm | about 400 μm | about 1–1.5 mm |
| Cylindrical | | | |
| Length | about 0.5–10 mm | about 1 mm | about 1.5 mm |
| Diameter | about 0.05–3 mm | about 600 μm | about 0.74 mm |
| Flat | | | |
| Length | about 0.5–10 mm | about 1 mm | about 2 mm |
| Width | about 0.5–10 mm | about 1 mm | about 1 mm |
| Thickness | about 0.1–1.0 mm | about 280 μm | about 0.3 mm |

[a] desired average daily dosage of 10 μg/day; drug loading of about 50 wt %
[b] desired average daily dosage of 15 μg/day drug loading of about 70 wt %

The configuration of the drug delivery system is determined by the location of the targeted oral tissue. For example, if the targeted tissue completely surrounds the drug delivery device, then several or all surfaces of the depot will ideally be therapeutic agent delivery surfaces. Typically, such a drug delivery device will be completely biodegradable. However, on occasion, the targeted tissue may be adjacent to only one side of the depot. In that instance, the face of the device that contacts the targeted tissue is designed to be the therapeutic agent delivery surface, while the opposing face of the depot can be covered with a therapeutic agent-impermeable layer to minimize diffusion of the therapeutic agent away from the targeted oral tissue. Such barrier layers would be positioned on the depot surface distal from the targeted tissue. The barrier layer would preferably be biodegradable, and would ideally degrade at a rate slower than that of the other system components.

C. Membrane

Additional structural features can be added to the system to control the rate of diffusion of the therapeutic agent from the system. For example, diffusion of the agent from the depot may be controlled by means of a drug-permeable membrane adjacent to the depot and positioned between the depot and the targeted tissue. The system could have a depot layer/membrane layer configuration or the system could have a central depot encased within the membrane layer, with these configurations being merely exemplary of the configurations that are suited to use in the invention.

The membrane may be composed of any of the materials described above, and will desirably have the same biodegradable or non-biodegradable characteristics as the depot material. In some systems, the depot will be saturated with therapeutic agent which results in a high release rate. One means of slowing the release of agent is be selecting a membrane material that is less permeable to the agent than the depot material is. In this instance, the lower agent-permeability characteristic of the membrane results in the agent remaining concentrated in the polymer. Thus, the overall rate of diffusion will be determined by the membrane's agent-permeability characteristics, which can allow for more controlled and/or extended delivery of the agent to the diseased tissue.

Exemplary non-biodegradable membrane materials include ethylene vinyl acetate, ethylene/vinyl alcohol, polyurethane, as well as polypropylene, polyethylene, nylon, polycarbonate, which are suited for use as microporous membranes; as well as blends of any of the foregoing. Exemplary preferred biodegradable materials are described above.

D. Backing Layer

When the controlled release drug delivery system comprises a depot as well as a membrane layer, it may be desirable for the system to include a backing layer. The backing layer is positioned on the surface(s) of the system that are not in contact with or adjacent to the targeted tissue. For example, when the system is configured as a sheet, the backing layer would typically be positioned on the side of the system most distal from the target tissue. The backing layer is preferably of a material which is impermeable to the therapeutic agent that is contained within the depot. The backing layer can be biodegradable or not, but will desirably have the same erodible or non-erodible characteristics as the depot material.

By including a backing layer in the system, the diffusion of agent from the depot will be limited to passage through the depot and/or the membrane layer. The backing payer can be made of any of the aforementioned biodegradable or non-biodegradable materials. Particularly suitable materials include, by way of illustration and not limitation, polyesters (e.g., Mylar®), polyethylene, polypropylene, halogenated polymers such as polytetrafluorethylene (e.g., Teflon®) and polychlorotrifluoroethylene (e.g., Aclar®) and other film materials as are well known in the art.

E. Adhesive Layer

In some embodiments of the invention, an adhesive layer can be included in the system to aid in securing the system at the desired site. Since the system in an intratissue system, the adhesive layer would facilitate initial placement of the system within the desired tissue. Preferably, the adhesive layer will be on the portion of the system that contacts with target tissue.

The adhesive layer may be composed of a bioadhesive, mucoadhesive and /or biocompatible pressure sensitive material. Exemplary adhesive materials include polyurethanes; acrylic or methacrylic resins, and their copolymers with other compounds; polyoxyethylenes; polyanhydrides; natural or synthetic rubbers; polyvinylacetate; poly (vinylpyrrolidone); cellulose derivatives; hyaluronic acid; chitosan; natural gums; and so forth. The adhesive may also include tackifiers, stabilizers or plasticizers (e.g., triethyl citrate, dibutylphthalate, diethylphthalate, acetyltriethyl citrate, tributyl citrate, acetyltetrabutyl citrate, triacetin, polyethylene glycol, castor oil), as are well known in the art.

F. Release Liner

The system (e.g., depot, membrane or adhesive layer) may be affixed to a release liner. The release liner, which may be of any suitable material which is impermeable to the therapeutic agent, serves to prevent or minimize diffusion of the agent out of the system during storage. In those embodiments where the system includes an adhesive layer, the release liner also serves to prevent the adhesive layer from adhering to materials during storage. Exemplary materials suited for use as the release liner include a silicone-coated or fluorocarbon-coated polyester film.

III. Methods of Treatment

The compositions and controlled release drug delivery system of the invention are useful for localized or targeted drug application into the desired intratissue placement site or target site by means of a trocar, punch biopsy or surgical incision. The invention also contemplates methods of treatment wherein forceps, for example are used to place the system in open wounds, surgically created cavities or cancerous tissue, or during any routine surgical manipulation.

The drug delivery system geometry and the application means are factors to consider based upon the particular disease being treated since the appropriate placement of the system and the final location helps to insure effective treatment of certain diseases. For example, when taking advantage of dexamethasone's effect on alkaline phosphotase activity, placement of the system should take into consideration whether the enzyme activity may vary among the specific tissue layers being considered for placement of the system.

Of particular interest is the treatment of diseases within the orofacial environment such as inflammation (both acute and chronic), infection and/or pain that is associated with periodontal disease, periodontal surgeries, root canal therapy, root canal surgery, extractions, oral surgeries, dental implants, cosmetic and facial surgery and temporomandibular joint syndrome or any surgery related to the ear, nose, eye and the brain. Such therapies are described in detail below. It is important to understand that several conditions may co-exist in that the patient may be experiencing inflammation and pain. The invention encompasses administering a therapeutic agent to reduce inflammation and a separate agent to alleviate pain. However, the invention also encompasses those methods where only the inflammation is treated, as a reduction in inflammation may bring about an alleviation of the accompanying pain symptoms.

The invention also relates to the treatment of diseases that originate in the orofacial environment. For example, the methods and systems of the invention can be used to prevent myocarditis in general, and in particular, to prevent infective and viral myocarditis. Infective myocarditis is often linked with periodontal surgery. It is therefore desirable to minimize or eliminate the number of pathogenic organisms in the periodontal tissue before the area is operated on and the pathogens have the opportunity to spread into the body, particularly to the heart. In this instance, an anti-infective agent can be delivered to the orofacial tissue, while preventing a systemic complication.

Typically the drug delivery system will be positioned at a placement site that is the same as the target site so as to provide targeted localized drug delivery. However, there are instances where it may be desirable to treat diseased tissue at a location that is distal from the placement site, in addition to or instead of treating the tissue at the placement site. For example, when treating the disease state of periodontitis, more than one tooth might be affected by the disease. One method might involve placement of a drug delivery system at each diseased tissue site. However, in a preferred method, a single drug delivery system would be positioned in the proximity of microvasculatory structures so that the released drug would be absorbed by the microvasculature in the vicinity of the system, which would then carry the drug to the diseased tissue. In another example, if drug delivery to the gingival tissue proximal to more than one tooth is desired, the placement of the drug delivery system can be selected nearby the target site in the vicinity of vessels responsible for gingival blood supply. Gingival blood supply originates from blood vessels in the periodontal ligament, the marrow spaces of the alveolar process and supraperiosteal blood vessels. These vessels in turn supply major capillary plexuses that are located in the connective tissue adjacent to the oral epithelium and the junctional epithelium. Other anatomical structures include glands, for example, lymph nodes and the corresponding drainage system.

The concept of agent diffusion or transport to different orofacial tissue sites is well understood. For example, in dental practice, anesthesia of teeth and gingival tissue is achieved either by infiltration or regional nerve block. In infiltration anesthesia, the anesthetic solution is injected into the area concerned, and the anesthetic agent diffuses through the tissues to anesthetize local nerve fibers. In regional nerve block the injection is given to affect the nerve(s) supplying the area, which may be at some distance from the operative site.

The bone of the alveolar part of the maxilla, especially that of the buccal (outer) surface, is relatively porous. Therefore, agents that can penetrate to the region of the apex of a tooth (where the root canal opens and the nerve enters the pulp) will effectively be administered to the tooth and surrounding gingiva. Similarly, treatment of the buccal aspect of the jaw is usually effective for all the upper teeth. For the teeth of the lower jaw, drug diffusion will likely only be effective for the incisors. The other mandibular teeth are embedded in bone that is denser and does not allow sufficient penetration of therapeutic agent; for these teeth, targeting the inferior alveolar nerve may be required. Accordingly, drug delivery systems can be placed strategically to take advantage of the surrounding microvasculature to carry the released therapeutic agents to the desired site. The advantage to common injections is that the drug delivery system delivery is extended and avoids the high spike (potential for local toxicity) and fast wash-out (non-therapeutic) typically experienced with common injections. The drug delivery systems of the invention can carry anesthetic or pain medication, for example, and can be placed at the usual injection sites to provide long-term pain relief.

Furthermore drug delivery can be directed to the peripheral nervous system in particular to the 12 pairs of cranial nerves in an attempt to alter or modify their principal function. These nerves are related to smell (olfactory), vision (optic), movement of the eye and constriction of the pupil and altering the curvature of the lens (oculomotor, trochlear, abducent), main sensor of the head and motor to the muscles of mastication and moving the lower jaw (trigeminal), motor to muscles of face, taste, parasympathetic for lacrimal, salivary and nasal glands (facial), taste and other sensory functions related to throat, control of blood pressure (glossopharyngeal), speech and swallowing (vagus), motor to the larynx, pharynx and soft palate (accessory) and moving the tongue (hypoglossal). In trigeminal neuralgia, pain occurs in numerous areas of the face where the branches of the nerve are distributed. Thus, the trigeminal nerve can be the target of local drug delivery of antiepileptic drugs or even muscle relaxants like chlorphenesin, which serve to mitigate the pain associated with trigeminal neuralgia.

Another structure that can be targeted for positioning of the drug delivery system of the invention, is the thyroid, where localized drug therapy may act to treat thyroid diseases such as hypo- and hyperthyroidism, Grave's and Hashimoto's disease, autoimmune thyroiditis, etc. Targeted delivery to the thyroid can be achieved by utilizing the superior thyroid artery, which branches from the external carotid artery right below the level of the greater cornu of the hyoid bone and ends in the thyroid gland. More specifically, the superior thyroid artery originates right under the anterior border of the ternocleidomastoideus. Covered by the skin it runs upward and forward, in the carotid triangle, arching downward beneath the Omohyoideus, Sternohyoideus, and Sternothyreoideus, distributing twigs to the adjacent muscles and to the external branch of the superior laryngeal nerve, which lie medial to it. Numerous branches reach the thyroid gland, anastomosing with its fellow of the opposite side, and with the inferior thyroid arteries. By utilizing the artery to carry the agent into the thyroid, one would eliminate the need for placing a drug delivery system inside the gland. On the other hand placing a triiodothyronine ("T3") or thyroxine ("T4") delivery system close to thyroid veins would allow the agents to be carried into the circulation. One example of targeting the thyroid is the treatment of Hashimoto's disease by delivering a glucocorticoid. Glucocorticoid therapy during the acute onset of the disease, in association with pain, alleviates the symptoms and improves the associated biochemical abnormalities, and has been shown to increase plasma T3 and thyroxine T4 levels by suppression of the autoimmune process. Long-term delivery of steroids in children may be administered via a local drug delivery system in an attempt to suppress antibody production and possibly to achieve a permanent remission. In general treatment of hypothyroidism, therapeutic delivery of T3 and T4 can be achieved with a local drug delivery system. In hyperthyroidism or Grave's disease the localized drug delivery is geared towards an overactive thyroid that is producing an excess of thyroid hormones. Glucocorticoids, like dexamethasone may be delivered via the local drug delivery system of the invention, to reduce thyroiditis. Localized antithroid drugs, like propylthiouracil or methimazole are also effective to block pathways leading to thyroid hormone production. In the case of lack of iodine, drug delivery can be geared towards preventing or the treatment of goiter.

Drug delivery to the sublingual gland and its related and surrounding tissues can be achieved by the Sublingual Artery, which branches off the lingual artery at the anterior margin of the Hyoglossus, running forward between the Genioglossus and Mylohyoideus to the sublingual gland. Its branches reach also the Mylohyoideus and neighboring muscles, as well as the mucous membrane of the mouth and gums. One of its branches continues behind the alveolar process of the mandible in the gum to anastomose with its opposing artery.

In another embodiment of the invention, the drug delivery system is placed in the vicinity of the Inferior Labial or Superior Labial Artery to provide drug to the lips and the surrounding mucous membrane, for example for the treatment of cold sores, to inhibit oral herpes (HSV1), or to relieve inflammation and pain that may occur with post herpetic neuralgia. The labial glands, the mucous membrane, and the muscles of the lower lip are supplied by the Inferior Labial Artery supplies, which arises near the angle of the mouth. From there it runs upward and forward under the Triangularis and penetrates the Orbicularis oris. Between this muscle and the mucous membrane, it follows a tortuous path along the edge of the lower lip to anastomoses with its opposing artery and with the mental branch of the inferior alveolar artery. The larger and more tortuous Superior Labial Artery supplies the upper lip. Along its course it branches off smaller vessels, which ascend to the nose; a septal branch ramifies on the nasal septum as far as the point of the nose, and an alar branch supplies the ala of the nose.

In another embodiment, the Deep Auricular Artery or the Anterior Tympanic Artery is utilized to supply the tympanic cavity or the temporomandibular joint. Both of these arteries branch off the first part (mandibular portion) of the internal maxillary artery. The Deep Auricular Artery passes through the parotid gland, behind the temporomandibular articulation, entering through the cartilaginous or bony wall of the external acoustic meatus and supplying the cuticular lining and the outer surface of the tympanic membrane, with branches to the temporomandibular joint. After piercing the petrotympanic fissure the Anterior Tympanic Artery circles around the membrane.

For the treatment of vertigo or prevention of motion sickness, drugs may be delivered to the postauricular region via the posterior auricular artery, which is a small branch from the external carotid that arises above the Digastricus and Stylohyoideus, opposite the apex of the styloid process. Under the parotid gland, it ascends on the styloid process of the temporal bone to the groove between the cartilage of the ear and the mastoid process, dividing into the auricular and occipital branches. The Auricular Branch runs behind the ear, beneath the Auricularis posterior, and is distributed to the back of the auricula, curving around the margin of the cartilage to supply the anterior surface.

In yet another embodiment, drug can be delivered to the root of the teeth, lips or structures of the mandible and mucous membrane of the mouth, by placing the drug delivery system along the Inferior Alveolar Artery and its subsequent divisions. The Inferior Alveolar Artery branches off the first part (mandibular portion) of the internal maxillary artery. Parallel to the inferior alveolar nerve it descends to the mandibular foremen on the medial surface of the ramus of the mandible. Running along side the nerve in the mandibular canal in the bone, it divides into two branches (incisor and mental) right opposite the first premolar tooth. Beneath the incisor teeth the incisor branch continues to run forward as far as the middle line, where it anastomoses with the opposing artery. At the mental foremen, the nerve and mental branch rise, the latter supplying the chin and anastomosing with the submental and inferior labial arteries. The lingual branch of the inferior alveolar artery descends with the lingual nerve and supplies the mucous membrane of the mouth. The several twigs of the inferior alveolar artery and the incisor branch enter the minute apertures at the extremities of the roots, and supply the pulp of the teeth.

Other drug delivery target structures can be, for example and not limited to, the brain (1-dopa in Parkinson's disease); inflamed nasal mucous membranes that are lining the passages of the nose due to, for example, seasonal allergic, perennial allergic, or perennial nonallergic rhinitis (antihistamines and/or steroids); eye muscles in exophthalmos, which is the condition in which one or both of the eyes bulge out of their sockets as a consequence of Grave disease, and which can cause loss of eye muscle control, double vision, and may require specialized treatment with steroids; and so forth.

One embodiment of the invention is a method of treating orofacial disease in a patient comprising the step of administering a drug delivery system within orofacial tissue, wherein the system comprises a semi-solid or solid depot and a therapeutically effective amount of at least one therapeutic agent and is within the range of about 0.03–17 mm$^3$ in size.

Another embodiment of the invention is a method of treating orofacial disease in a patient comprising the step of administering a drug delivery system within orofacial tissue, wherein the system comprises a semi-solid or solid depot and a therapeutically effective amount of an anti-inflammatory agent.

One skilled in the art and having a fundamental understanding of the cardiovascular system, in particular the arteries of head and neck (external carotid), can readily ascertain how to position a drug delivery system of the invention, in such a manner so as to deliver therapeutic agent to the desired target tissue in the orofacial environments. Specific applications of these methods are set forth below.

A. Treatment of Periodontal Disease

The methods and drug delivery systems described herein find utility in treating periodontal disease in its various stages. Early periodontal disease occurs when bacterial plaque accumulates along the gum line, the periodontal tissue, and periodontium in particular, becomes inflamed, resulting in a condition known as gingivitis. If left untreated, the inflammation associated with early periodontal disease can result in the gingival tissue pulling away from the teeth, which then allows for the formation of periodontal pockets that become a depository for bacteria, tartar, food debris, and so forth. In its advanced stage, periodontal disease can result in the formation of painful gum abscesses. However, most detrimentally, continued inflammation of the periodontium leads to a visibly receding gum line and eventually to a critical bone loss. As a result the teeth can become loose and ultimately may be lost.

For the treatment of periodontal disease and the resulting tissue and bone loss, the systems of the invention would typically be positioned within gingival vestibular mucosal tissue for targeted drug delivery to the diseased supporting periodontal tissue (periodontal ligament, bone tissue and gingival tissue). In another embodiment, the drug delivery system can be positioned inside the attached gingival and an anti-inflammatory agent can be delivered to the periodontal tissue for arresting the deterioration due to host response complications caused by periodontal disease and to further promote the regeneration of the destroyed and/or lost tissue. Such systems can be formulated to provide delivery of an anti-inflammatory agent within the range of about 5–50 µg/day, for a time period of 7–90 days.

In addition to the delivery of anti-inflammatory agents, such as dexamethasone, the systems of the invention can be formulated to provide delivery of a tissue and bone growth factor within the range of about 5–50 µg/day, for a time period of 7–90 days and would typically be positioned within gingival vestibular mucosal tissue for targeted drug delivery to the regenerating bone tissue location.

It has also been found that specific anaerobic bacteria in the periodontal pockets are initiators of periodontal disease. Therefore, it may be desirable to utilize the systems of the invention to provide intragingival tissue delivery of an anti-infective agent, particularly those having MIC or MBC values on the average less than about 5 µg/ml for the bacterial species of interest, within the range of about 5–25 µg/day, for a time period of 3–14 days. For the common susceptible organisms found in periodontal disease anti-infective agents can be administered for effective treatment. These include, for example, aminoglycosides such as gentamycin and tobramycin; dicloxacillin; fluoroquinolones such as ciprofloxacin; glycopeptides such as vancomycin; lincosamides such as clindamycin; macrolides such as azithromycin and erythromycin; nitroimidazoles such as metronidazole; oxacillin; penicillins; tetracyclines; and so forth.

The indirect effects mediated by the host's reaction to the bacteria primarily cause the actual destruction of the periodontal tissue. Bacterial metabolites induce leucocyte chemotaxis, which results in the inflammatory cells accumulating at the site of the bacterial challenge. Furthermore, bacterial metabolites induce the production of inflammatory mediators by leucocytic cells, in particular monocytes. Amongst these are local disease mediators such as metabolites of arachidonic acid, e.g. leukotrienes, prostaglandins and thromboxanes. Additionally, the loss of alveolar bone may be directly induced by pathogenic metabolites of bacteria, in particular proteolyte enzymes. Prostaglandins have been found to be particularly important in the metabolism and destruction of tissue and alveolar bone. Prostaglandins and thromboxanes are formed from arachidonic acid by an enzyme cascade, the first step of which is the cyclo-oxygenation by an enzyme called cyclo-oxygenase. Inhibiting the cyclo-oxygenase would inhibit the formation of prostaglandins and thus reduce alveolar bone loss. For that reason, delivery of glucocorticosteroids such as dexamethasone are particularly useful in the treatment of periodontal disease. In addition, dexamethasone not only provides anti-inflammatory and pain reducing benefits, but also up-regulates alkaline phosphatase activity in regenerating human periodontal cells and thereby promotes the tissue regenerating process, which is essential in the treatment of periodontal disease. Re-attaching gingival tissue to the regenerated bone eliminates the periodontal pocket, the preferred location for bacteria re-colonization that would continue or restart the periodontal disease process.

B. Treatment of Acute and Chronic Inflammation

The methods and drug delivery systems described herein find utility in treating both acute and chronic inflammation of orofacial tissue. Acute inflammation can be due to factor such as mechanical teeth cleaning (including root planning and scaling), oral surgery, periodontal surgery to cut down the periodontal pocket flap, apicoectomy, root canal procedure, a 3rd molar extraction procedure, any surgery to repair nose, ear or eye problems, and so forth, resulting in inflammation of manipulated tissues. For the treatment of acute inflammation, the systems of the invention would typically be positioned within the inflamed tissue or the location of the surgical operation for targeted drug delivery to inflamed tissue surrounding the surgical or manipulated site. Such systems can be formulated to provide delivery of an anti-inflammatory agent within the range of about 5–50 µg/day, for a time period of 3–14 days. The administration of an anti-inflammatory agent post-surgically in this manner, will also serve to reduce pain, edema, scarring, and other complications resulting from the oral, nose, eye or ear surgery, as well as reduce inflammation. In addition, to prevent infection due to pre-existing or bacteria introduced during the surgery an anti-infective agent can be co-delivered, as well as an additional pain medication for the treatment or prevention of excessive pain.

More specifically, if the treatment of acute inflammation and pain, associated with a teeth cleaning procedure, scaling and root planing, or any other periodontal surgery, is desired the systems of the invention would typically be positioned within gingival vestibular mucosal tissue (preferably distally and buccally) not more than 10–15 mm away from the manipulated tissue or within the surgical opening before closure. Such systems can be formulated to provide delivery of an anti-inflammatory agent within the range of about 5–50 µg/day, for a time period of 3–7 days.

Chronic inflammation can be due to factors, including on-going tissue decay due to periodontal disease, temporomandibular joint syndrome, placement of devices for facilitating tooth movement or providing orthodontic support, seasonal allergic, perennial allergic, or perennial nonallergic rhinitis, resulting in inflammation of the nasal mucosa. Chronic inflammation can also be the result of an underlying systemic disease such as Hashimoto's disease. For the treatment of chronic inflammation, the systems of the invention would typically be positioned within the inflamed tissue for targeted drug delivery to inflamed tissue. Such systems can be formulated to provide delivery of an anti-inflammatory agent within the range of about 5–50 µg/day, for a time period of 14–90 days.

The methods and systems of the invention can also be designed to treat both acute and chronic inflammation with a single system. The system would typically be positioned within the inflamed tissue for targeted drug delivery to inflamed tissue. Such systems can be formulated to first provide delivery of an anti-inflammatory agent within the range of about 5–50 µg/day, for a time period of 5–10 days, followed by delivery of an anti-inflammatory agent within the range of about 2–25 µg/day, for a time period of at least one month, and up to 3 months. The higher 5–50 µg/day dose for the initial short time period of 5–10 days is directed at treatment of acute inflammation, while the lower 2–25 µg/day dose for the subsequent longer time period of up to 3 months is directed at treatment of chronic inflammation. Such a dosing regimen is particularly suited for administration of a anti-inflammatory agent such as dexamethasone for treatment of acute and chronic inflammation in the context of periodontal disease, since dexamethasone serves as a pain and anti-inflammatory medicine in the initial state of the delivery (acute inflammation after periodontal cleaning procedure) and also treats the underlying chronic inflammation (host response reaction) as well as facilitates tissue regeneration by stimulating ALP activity.

In addition, the local administration of an anti-inflammatory agent to a diseased tissue structure can have also other benefits. For example, a drug delivery system placed to deliver dexamethasone to the cochlea suppresses the autoimmune response that is thought to be associated with Meniere's disease. Additional therapeutic agents such as anti-emetic, anti-nausea and anti-vertigo drugs may be delivered to treat the symptoms of Meniere's disease. Local administration of anti-inflammatory agents also affects allergic rhinitis symptoms. For example corticosteroids have been shown to have a wide range of effects on multiple cell types (e.g., mast cells, eosinophils, neutrophils, macrophages, and lymphocytes) and mediators (e.g., histamine, eicosanoids, leukotrienes, and cytokines) involved in inflammation.

C. Prevention or Treatment of Infection

The methods and drug delivery systems described herein find utility in preventing or treating infection in orofacial tissue. Infections are often associated with surgical procedures such as an apicoectomy, a root canal procedure, or a 3rd molar extraction, either as an existing condition or a condition that can arise after the patient has undergone the specific procedure, as well as being associated with periodontal disease, resulting in infection of manipulated tissue. Anti-infective agents such as aminoglycosides such as gentamycin and tobramycin; dicloxacillin; fluoroquinolones such as ciprofloxacin; glycopeptides such as vancomycin; lincosamides such as clindamycin; macrolides such as azithromycin and erythromycin; nitroimidazoles such as metronidazole; oxacillin; penicillins; and tetracyclines; are preferably administered.

For both prophylactic treatment of such infections as well as the treatment of existing infections, the systems of the invention would typically be positioned within the tissue that is susceptible to becoming infected or which is already infected, for targeted drug delivery to the susceptible or infected tissue. Such systems can be formulated to provide delivery of an anti-infective agent within the range of about 5–50 µg/day, for a time period of 3–30 days.

D. Treatment of Pain

The methods and drug delivery systems described herein find utility in treating pain in orofacial tissue. Pain can be due to numerous factors, such as an underlying disease (e.g., periodontal disease, cranomandibular disease such as temporomandibular joint syndrome, etc.) or a surgical or other procedure (e.g., placement of devices for facilitating tooth movement or providing orthodontic support, root scaling and planning, stapedectomy, tonsillectomy, elective surgery or reconstructive surgery to repair tissues damaged in accidents, etc.). For the treatment of pain, the systems of the invention would typically be positioned within the affected tissues or within the open wound before closure for targeted drug delivery to the particular pain receptors. Such systems can be formulated to provide delivery of a pain management medication within the range of about 5–50 µg/day, for a time period of 3–30 days. Since alleviation of inflammation often results in a reduction in pain, such systems can also be formulated to provide delivery of an anti-inflammatory agent within the range of about 5–50 µg/day, for a time period of 3–30 days.

E. Treatment of Tissue or Bone Loss

Tissue and/or bone loss can be due to numerous factors, including periodontal disease, the wearing of a prosthesis, removal of cancerous tissue and structures, an accident, etc. The treatment of tissue or bone loss can involve reducing the amount of such destruction and/or facilitating tissue or bone growth. Accordingly, the methods and drug delivery systems described herein find utility in treating tissue or bone loss in restoration surgery, aesthetic surgery practices, apicoectomies, $3^{rd}$ molar extraction, tooth extraction in general to rebuild bone material for implant placement (facilitate osseointegration process), extraction, periodontal tissue regeneration, surgery that causes tissue or bone loss such as the surgical removal of cancerous lesions, anti-wrinkle treatment (Botox, vitamin C, etc), and so forth. For the treatment of tissue and/or bone loss, the systems of the invention would typically be positioned within the surgical lesion or open wound right before closure or place within or close to the to be treated tissue. Such systems can be formulated to provide delivery of a tissue or bone growth factor or agents that promote bone or tissue regeneration within the range of about 2–50 µg/day, for a time period of 7–90 days.

In another embodiment of the invention, the methods and drug delivery systems described herein find utility in treating orofacial diseases, in combination with a device for facilitating tooth movement or providing orthodontic support. Instead of regenerating bone tissue, the systems of the invention would be positioned in front of a tooth or teeth that are desired to be moved to, for example, align and adjust the bit of a patient. Such systems can be formulated to provide delivery of an agent that alters bone constitution (e.g. bone alteration agents such as prostaglandin) within the range of about 2–50 µg/day, for a time period of about 7–60 days.

F. Treatment of Cancer and Cancer-Related Disorders

The methods and drug delivery systems described herein find utility in treating cancer and cancer-related disorders of orofacial tissue. Orofacial tissue cancers or cancers of the head and neck can be grouped together in relation to their position in the body. Cancers of the oral cavity are those which develop on the lips or in the mouth itself. More specifically, cancers of the oral cavity can occur inside the mouth in the tongue, the hard palate, the gums, the floor of the mouth and the inner lining of the lips and cheeks (sometimes referred to as the buccal mucosa). Oropharyngeal cancer develops in the oropharynx, the part of the throat that sits directly behind the mouth and includes the soft palate, the base of the tongue, the side walls of the throat, where the tonsils are located and the back wall of the throat (also called the posterior pharyngeal wall). Cancer of the nose can develop in the skin of the nostril and the lining of the nose, the nasopharynx (nasopharyngeal carcinoma), and in the air spaces in the bones of the face alongside the nose (paranasal sinuses). Cancers can also develop in the linings of these areas. Cancer of the ear typically develop in the skin of the ear, and more rarely occur in the structures deep inside the ear. Cancer is the eye itself is unusual, but can develop in the skin of the eyelids (ocular melanoma). Occasionally, cancer of the lymph nodes, lymphoma, can develop behind the eye. Other cancers of the head and neck area include cancers of the thyroid gland, larynx (voicebox), salivary glands and brain.

For the treatment of cancer, the systems of the invention would typically be positioned within the cancerous tissue or close to vasculature that would convectively carry the drug into the cancerous tissue for targeted drug delivery to the cancerous tissue. Alternately, the drug can be targeted to the vasculature supporting the cancerous tissue so as to focus on primarily killing the vasculature. Such systems can be formulated to provide delivery of an antineoplastic agent within the range of about 5–50 µg/day, for a time period of 7–30 days.

In addition, the methods and systems described herein find utility in treating chemotherapy or radiotherapy induced oral mucositis, which is inflammation and ulceration of the lining of mouth, the throat and/or the gastrointestinal tract. The system of the invention can be positioned within the orofacial tissue near the vasculature, i.e., near the arterial supply. In this manner, localized delivery of anti-inflammatory agents would treat the inflammation and ulceration of the mouth lining and throat. The systems of the invention can be formulated to deliver within the range of about 5–50 µg/day of an anti-inflammatory agent such as a glucocorticoid, for a time period of about 7–30 days. The systems of the invention are preferably formulated to deliver dexamethasone within the aforementioned range and time frame.

G. Treatment of Glandular Disorders

The methods and drug delivery systems described herein find utility in treating orofacial diseases related to malfunctioning glands or disease of the glands including tumors, pleomorphic adenoma, dry mouth, drooling; any gland destruction by for example an autoimmune disease such as Sjogrens syndrome, etc.; pain, infection, and/or inflammation due to surgery to repair glands (diversion of ducts, stone removal, etc.).

In addition, the three major glands: the bilateral sublingual and submandibular glands (both open into the floor of mouth, one on each side of the frenulum of the tongue) and parotid can be used to carry therapeutics agents delivered to them into areas the typically serve. Therapeutic agent delivery includes fluoride (prevention of cavities); anti-inflammatory agents (mucositis, etc.), anti-infectives (halitosis), compounds that aid the ingestion process by therapeutic agent spiked saliva that moistens and lubricates the food and agents influence the peristalsis to the stomach (esophagitis, problems with swallowing, etc.).

These drug delivery access areas can also be used to deliver therapeutic agents slowly and for extended periods to the upper regions of the esophagus. For example, Barrett's esophagus is a condition that develops in some people who have chronic gastroesophageal reflux disease (GERD) or inflammation of the esophagus (esophagitis). In Barrett's esophagus, the normal cells that line the esophagus (squamous cells) are damaged by acid reflux from GERD resulting in abnormal changes. Other minor glands such as lingual, labial, tonsillar and buccal maybe be used for more area targeted delivery.

EXAMPLES

The practice of the present invention will employ, unless otherwise indicated, conventional techniques of pharmaceutical formulation, medicinal chemistry, and the like, which are within the skill of the art. Such techniques are explained fully in the literature. The following examples are put forth so as to provide those of ordinary skill in the art with a complete disclosure and description of how to make and use the systems of the invention, and are not intended to limit the scope of what the inventor regard as the invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All components are obtainable commercially unless otherwise indicated.

Example 1

Large microparticles are prepared using the solvent evaporation process. Briefly, in the solvent-evaporation process, a polymer solution containing the drug is emulsified in a second phase to create small droplets. A variety of different agitation techniques can be used. The second or continuous phase consists of an emulsifier in a low volatile and preferably poor solvent for the components of the first phase. During the evaporation of the highly volatile solvent of the first phase, the polymer and drug-containing droplets solidify. These formed microparticles are then separated by filtration from the continuous phase solvent and washed to remove remaining emulsifier. If water is the continuous phase solvent, agents with high water solubility can be lost in significant amounts during this procedure. Aqueous phase volume, vessel and stirrer geometry, stir rate, concentration of emulsifier, volume and viscosity of oil phase, etc. are all important factors that influence the final particle size distribution, while the polymer depot material to drug ratio and the polymer depot chemistry define the biodegradation and agent release rate.

A predetermined amount of the drug dexamethasone (3.3 g) is added to the oil phase (polymer in solvent 5 g/8 g). The polymer is 50/50 polylactic acid/glycolic acid with a molecular weight of about 20,000 g/mol, and the solvent is methylene chloride. The aqueous phase (23.5 g) contains the emulsifier polyvinyl alcohol (2.5 g) to adjust the viscosity. Approximately 3 drops of octanol are added to the aqueous phase to prevent or minimize foaming. Furthermore, to prevent drug loss into the aqueous phase, the aqueous phase is saturated with the drug.

An I-inch impeller mixer is used to agitate the continuous phase at about 700 rpm. Then the oil phase is slowly added to the aqueous phase. This mixture is stirred for about an hour, and air is passed over it to remove the evaporating solvent. At about 30 minutes most of the methylene chloride will have evaporated and the emulsion droplets solidified. Agitation is continued at about 60 rpm for another 45 minutes to prevent agglomeration. The solidified microparticles then are separated from the aqueous solution using a vacuum funnel and filter paper. After continued washing to remove any emulsifier the microparticles are dried, sieved and only particles larger than 500 microns are kept.

Measuring in vitro Drug Release

Large microparticles of about 330 micron radius from Example 1 are placed into screw cap glass vials filled with 10 ml of aqueous saline solution (0.9% NaCl) and placed into a shaking water bath kept at a temperature of 37° C. Samples of 8 ml are periodically removed and replaced with same amount of fresh saline. The samples are then analyzed by HPLC (USP method) for their drug concentration. A typical drug release characteristic is shown in the following table:

| Time of measurement | Cumulative Drug released (mg) |
| --- | --- |
| Day 1 | 25 |
| Day 2 | 35 |
| Day 4 | 50 |
| Day 7 | 61 |

The drug delivery system can provide a high initial drug release. This is desirable, for example, to prevent inflammation flare-up and the associated edema, etc. after a surgical procedure. Prevention of inflammation will also prevent or minimize post-surgical pain. Subsequent drug release would be lower, but remains fairly steady until about 7 days when the theoretical drug load is reached. During this phase, lower drug delivery would be sufficient to maintain a therapeutically effective anti-inflammatory drug level.

Example 2

As described in Example 1 microparticles of 500 microns and larger are made using the anti-infective ciprofloxacin. A typical drug release characteristic is shown in the following table:

| Time of measurement | Cumulative Drug released (mg) |
| --- | --- |
| Day 1 | 29 |
| Day 2 | 42 |
| Day 4 | 53 |
| Day 7 | 59 |

The drug delivery system can provide a high initial release which would, in the clinical environment, generate locally high anti-infective concentrating levels. This is desirable, for example after surgery, to prevent microorganisms that may be introduced during the surgical procedure from replicating and causing an infection of the wound area. The subsequent drug release would be lower, which is sufficient to generate an in vivo maintenance level that can prevent the microbial re-colonization of the surgical area. At day 7 the cumulative drug release would equal the theoretical drug-loading amount.

Example 3

For the preparation of disc-shaped drug delivery systems, 2 grams of Pharmacoat®606 (hydroxypropylmethylcellulose commercially available from Shin-Etsu) is wetted with 2 grams of water. To that paste is added 3 grams of microparticles from Example 1, from the size fraction range of 250 to 500 microns. After thorough mixing the resulting paste is then molded into a flat film of 1 mm thickness using a carver press. The pressed film is then cut into 1, 2 and 5 $mm^2$ discs using thin walled Teflon straws. The discs are then dried overnight in a vacuum oven.

Example 4

For the preparation of disc-shaped drug delivery systems, 2 grams of Metolose SR (90SH, 100000SR, methylcellulose commercially available from Shin-Etsu) is wetted with 2 grams of water. To that paste is added 2 grams USP dexamethasone. After thorough mixing the resulting paste is then molded into a flat film of 1 mm thickness using a carver press. The pressed film is then cut into 1, 2 and 5 $mm^2$ discs using thin walled Teflon straws. The discs are then dried overnight in a vacuum oven.

Example 5

For the preparation of disc-shaped drug delivery systems, 2 grams of Metolose SR is wetted with 2 grams of water. To that paste is added 3.6 grams USP vancomycin. After thorough mixing the resulting paste is then molded into a flat film of 1 mm thickness using a carver press. The pressed film is then cut into 1, 2 and 5 $mm^2$ discs using thin walled Teflon straws. The discs are then dried overnight in a vacuum oven.

Example 6

For the preparation of disc-shaped drug delivery systems, 2 grams of L-HPC (LH-20, low-substituted hydroxypropylcellulose commercially available from Shin-Etsu) is wetted with 2 grams of water. To that paste is added 3.6 grams USP vancomycin. After thorough mixing the resulting paste is then molded into a flat film of 1 mm thickness using a carver press. The pressed film is then cut into 1, 2 and 5 $mm^2$ discs using thin walled Teflon straws. The discs are then dried overnight in a vacuum oven.

Example 7

For the preparation of disc-shaped drug delivery systems, 2 grams of L-HPC is wetted with 2 grams of water. To that paste is added 2 grams USP dexamethasone. After thorough mixing the resulting paste is then molded into a flat film of 1 mm thickness using a carver press. The pressed film is then cut into 1, 2 and 5 mm² discs using thin walled Teflon straws. The discs are then dried overnight in a vacuum oven.

Example 8

For the preparation of disc-shaped drug delivery systems, 2 grams of AQOAT Enteric Coating Agent (AS/HF, hydroxypropylmethyl cellulose acetate succinate commercially available from Shin-Etsu) is wetted with 2 grams of water. To that paste is added 1.5 grams USP dexamethasone and 1.5 g of vancomycin. After thorough mixing the resulting paste is then molded into a flat film of 1 mm thickness using a carver press. The pressed film is then cut into 1, 2 and 5 mm² discs using thin walled Teflon straws. The discs are then dried overnight in a vacuum oven.

Example 9

For the preparation of disc-shaped drug delivery systems, 2 grams of gelatin (Norland High Molecular Weight Fish Gelatin, Food/Pharmaceutical Grade) is wetted with 2 grams of water. To that paste is added 1.5 grams USP dexamethasone and 1.5 g of USP vancomycin. After thorough mixing the resulting paste is then molded into a flat film of 1 mm thickness using a carver press. The pressed film is then cut into 1, 2 and 5 mm² discs using thin walled Teflon straws. The discs are then dried overnight in a vacuum oven.

Example 10

For the preparation of disc-shaped drug delivery systems, 2 grams of gelatin (Norland High Molecular Weight Fish Gelatin, Food/Pharmaceutical Grade) is wetted with 2 grams of water. To that paste is added 1.5 grams USP dexamethasone and 1.5 g of USP ciprofloxacin. After thorough mixing the resulting paste is then molded into a flat film of 1 mm thickness using a carver press. The pressed film is then cut into 1, 2 and 5 mm² discs using thin walled Teflon straws. The discs are then dried overnight in a vacuum oven.

Example 11

A saturated solution of hyaluronic acid in water is prepared. Micronized S(-)ketorolac is added to achieve a mixture having a polymer to drug ratio of 40:60. The resulting mixture is poured on a glass plate covered with a standard silicone coated polyester release liner. A gardener knife is used to create a 300 mm thick film. The glass plate with the resulting film is placed into a vacuum oven and dried overnight at 80° C. The resulting film is cut into strips of 1.5 mm by 3 mm.

Example 12

A saturated solution of gelatin (Norland High Molecular Weight Fish Gelatin, Food/Pharmaceutical Grade) in water is prepared. Micronized clindamycin is added to achieve a mixture having a polymer to drug ratio of 50:50. The resulting mixture is poured on a glass plate covered with a standard silicone coated polyester release liner. A gardener knife is used to create a 300 mm thick film. The glass plate with the resulting film is placed into a vacuum oven and dried overnight at 80° C. The resulting film is cut into strips of 1.5 mm by 3 mm.

Example 13

A saturated solution of hyaluronic acid in water is prepared. Micronized R(-)methadone is added to achieve a mixture having a polymer to drug ratio of 40:60. The resulting mixture is poured on a glass plate covered with a standard silicone coated polyester release liner. A gardener knife is used to create a 300 mm thick film. The glass plate with the resulting film is placed into a vacuum oven and dried overnight at 80° C. The resulting film is cut into strips of 1.5 mm by 3 mm.

Example 14

The drug delivery systems can also be manufactured by the extrusion method. This is preferred in those instances where the therapeutic agent is heat-stable at temperatures below 100° C., but contact with solvents is not desired. Preferred depot polymers include polymers with low glass transition temperature or low melting point, preferably in the range below 70° C. or thereabout or temperature lower then the temperature that would cause harm to the agent.

In general, the polymers to form the depot are thoroughly pre-mixed with the agent(s) and extruded through an orifice of desired geometry. Depending upon the design of the extrusion apparatus, the mixing process can also be part of the extrusion process where appropriate screw geometry assures optimum mixing. The extruder orifice can have different shapes, including a round opening allowing the formation of a cylinder-like extrusion product, a flat orifice to form sheet-like extrusion product, etc. To minimize or prevent the fine powder explosion potential during the mixing and handling while preparing the embodiments of this invention, flame suppressant materials, like ethyl cellulose (Island Pyrochemical Industries) can be incorporated into the mix. Other inactive depot materials may be introduced to improve adhesion to the placement tissue (gelatin, hyaluronic acid, cellulosics, etc.) or to improve the flowability of the melt through the extrusion orifice.

Two grams of well-mixed powder of active and inactive materials at a ratio of 50:50 are prepared. The active agent is dexamethasone and the biodegradable polymer is a 50:50 polylactic acid/polyglycolic acid copolymer with an average molecular weight of 17,000 g/mol. The well-mixed powder is filled into a batch extruder and heated for 1 hour at 95° C. The melt is then extruded through a circular orifice to create a filament of 0.46 mm diameter. From the filament various length sub-units are cut and tested in in vitro drug release tests as described in Example 1. A typical drug release characteristic of a 1.2 mm long drug delivery system is shown in the following table:

| Time of measurement | Cumulative Drug released (mg) |
| --- | --- |
| Day 1 | 35 |
| Day 2 | 52 |
| Day 4 | 77 |
| Day 7 | 98 |

Example 15

Two grams of well-mixed powder of active and inactive materials at a ratio of 70:30 is prepared. The active agent is dexamethasone and the biodegradable polymer is a 50:50 polylactic acid/polyglycolic acid copolymer with an average molecular weight of 50,000 g/mol. The well-mixed powder is filled into a batch extruder and heated for 1 hour at 115° C. The melt is then extruded through a circular orifice to create a filament of 1.1 mm diameter. From the filament various length sub-units are cut and tested in in vitro drug release tests as described in Example 1. A typical drug release characteristic of a 3 mm long drug delivery system is shown in the following table:

| Time of measurement | Cumulative Drug released (mg) |
| --- | --- |
| Day 1 | 290 |
| Day 2 | 420 |
| Day 4 | 589 |
| Day 7 | 821 |
| Day 14 | 1160 |
| Day 21 | 1478 |
| Day 28 | 1666 |
| Day 35 | 1824 |
| Day 42 | 1934 |

Example 16

Extruded filament sections from Example 15 (10-cm length) are overcoated with a thin film of an additional polymer. This is achieved by dipping the selected filament sections into a 3-wt % aqueous solution of Pharmacoat®615 (Shin-Etsu). The coated filament sections are then dried overnight in a vacuum oven at room temperature. From the overcoated filaments various length sub-units are cut and tested in in vitro drug release tests as described in Example 1. A typical drug release characteristic of a 3 mm long drug delivery system is shown in the following table:

| Time of measurement | Cumulative Drug released (mg) |
| --- | --- |
| Day 1 | 98 |
| Day 2 | 159 |
| Day 4 | 286 |
| Day 7 | 467 |
| Day 14 | 807 |
| Day 21 | 1112 |
| Day 28 | 1389 |
| Day 35 | 1597 |
| Day 49 | 1956 |

The overcoated drug delivery systems can provide a reduced initial drug release (burst effect) and a closer to zero-order average drug release with a slightly extended drug delivery interval.

Example 17

To establish a lower permeability coating for the extruded filament sections of Example 15 (10-cm length), EASTMAN Cellulose Acetate (CA-398-10NF) is used. The permeability of cellulose acetate films can be chemically adjusted by varying the acetyl content. As the amount of acetyl increases, the permeability decreases and solvent resistance and glass transition temperature increases. The filaments are dipped in a 0.5 wt % CA-398-10NF solution in acetone and dried overnight under vacuum. Drug release from such systems can be extended to 3 months.

Example 18

Two grams of well-mixed powder of active and inactive materials at a ratio of 50:50 is prepared. The active agent is S(−)ketorolac and the biodegradable polymer is a 50:50 polylactic acid/polyglycolic acid copolymer with an average molecular weight of 20,000 g/mol. The well-mixed powder is filled into a batch extruder and heated for 1 hour at 115° C. The melt is then extruded through a circular orifice to create a filament of 0.46 mm diameter. Sub-units of various length are cut from the filament.

Example 19

Two grams of well-mixed powder of active and inactive materials at a ratio of 60:40 is prepared. The active agent is R(−)methadone and the biodegradable polymer is a 50:50 polylactic acid/polyglycolic acid copolymer with an average molecular weight of 45,000 g/mol. The well-mixed powder is filled into a batch extruder and heated for 1 hour at 115° C. The melt is then extruded through a circular orifice to create a filament of 0.9 mm diameter. Sub-units of various length are cut from the filament.

Example 20

Two grams of well-mixed powder of active and inactive materials at a ratio of 50:50 is prepared. The active agent is clindamycin and the biodegradable polymer is a 50:50 polylactic acid/polyglycolic acid copolymer with an average molecular weight of 20,000 g/mol. The well-mixed powder is filled into a batch extruder and heated for 1 hour at 1 15° C. The melt is then extruded through a circular orifice to create a filament of 0.46 mm diameter. Sub-units of various length are cut from the filament.

Example 21

Two grams of well-mixed powder of active and inactive materials at a ratio of 80:20 is prepared. The active agent is ganciclovir and the biodegradable polymer is a 50:50 polylactic acid/polyglycolic acid copolymer with an average molecular weight of 50,000 g/mol. The well-mixed powder is filled into a batch extruder and heated for 1 hour at 110° C. The melt is then extruded through a circular orifice to create a filament of 1.1 mm diameter. The extruded filament sections are dipped into a 3-wt % aqueous solution of Pharmacoat®615. The coated filament sections are then dried overnight in a vacuum oven at room temperature. Sub-units of various length are cut from the overcoated filament.

Example 22

Two grams of well-mixed powder of active and inactive materials at a ratio of 80:20 is prepared. The active agent is thyroxine (T4) and the biodegradable polymer is a 50:50 polylactic acid/polyglycolic acid copolymer with an average molecular weight of 40,000 g/mol. The well-mixed powder is filled into a batch extruder and heated for 1 hour at 95° C. The melt is then extruded through a circular orifice to create a filament of 1.1 mm diameter. The extruded filament sections are dipped into a 3-wt % aqueous solution of Pharmacoat®615. The coated filament sections are then dried overnight in a vacuum oven at room temperature. Sub-units of various length are cut from the overcoated filament.

Example 23

For the preparation of disc-shaped drug delivery systems, 2 grams of Metolose SR are wetted with 2 grams of water. To that paste is added 2 grams USP lidocaine. After thorough mixing the resulting paste is then molded into a flat film of 1 mm thickness using a carver press. The pressed film is then sprayed on one side with a solution of 0.5 wt % CA-398-10NF solution in acetone. Strips of 3 mm by 5 mm are cut and dried overnight in a vacuum oven.

Example 24

The vitamin E ester d-α-tocopheryl acetate is mixed with dexamethasone powder in a ratio of 50:50 and then extruded through a round orifice (0.5 mm) at a temperature of 50° C. The melt is then sub-divided into dosage units of various lengths and cooled overnight.

Example 25

The vitamin E ester d-α-tocopheryl succinate is mixed with dexamethasone powder in a ratio of 50:50 and then extruded through a round orifice (0.5 mm) at a temperature of 90° C. The melt is then sub-divided into dosage units of various lengths and cooled overnight.

Each of the patents, publications, and other published documents mentioned or referred to in this specification is herein incorporated by reference in its entirety.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention.

Accordingly, the scope of the invention should therefore be determined with reference to the appended claims, along with the full range of equivalents to which those claims are entitled.

We claim:

1. A method of treating disease in or originating in the orofacial environment in a patient comprising the step of administering a drug delivery system within orofacial tissue, wherein the system comprises a semi-solid or solid depot and a therapeutically effective amount of at least one therapeutic agent contained therein, and is within the range of about 0.03–17 mm³ in size, and wherein the therapeutic agent comprises about 30–95 wt% of the depot.

2. The method of claim 1 wherein the depot is biodegradable.

3. The method of claim 2 wherein the system is implanted by a punch biopsy procedure.

4. The method of claim 2 wherein the system is inserted with a trocar.

5. The method of claim 2 wherein the system is inserted after a surgical incision.

6. The method of claim 1 wherein the depot is non-biodegradable.

7. The method of claim 6 wherein the system is implanted by a surgical incision.

8. The method of claim 1 wherein the therapeutic agent is selected from the group consisting of anti-inflammatory agents, anti-infective agents, tissue and bone growth factors, pain management medication, antineoplastic agents, bone alteration agents, thyroid drugs, and combinations thereof.

9. The method of claim 1 which further comprises administering one or more additional therapeutic agents.

10. The method of claim 9 wherein the one or more additional therapeutic agents are contained within the drug delivery system.

11. The method of claim 9 wherein the one or more additional therapeutic agents are contained within additional drug delivery systems, each comprising a semi-solid or solid depot and a therapeutically effective amount of the therapeutic agent contained therein, and having a size within the range of about 0.03–17 mm³.

12. The method of claim 9 wherein the additional therapeutic agents are selected from the group consisting of anti-inflammatory agents, anti-infective agents, tissue and bone growth factors, pain management medication, antineoplastic agents, bone alteration agents, thyroid drugs, and combinations thereof.

13. The method of claim 1 wherein the drug delivery system delivers therapeutic agent at a rate of about 5–50 µg per day.

14. The method of claim 13 wherein the drug delivery system delivers therapeutic agent at a rate of about 5–35 µg per day.

15. The method of claim 14 wherein the drug delivery system delivers therapeutic agent at a rate of about 7–15 µg per day.

16. The method of claim 1 wherein the drug delivery system delivers therapeutic agent for at least about 3 days.

17. The method of claim 16 wherein the drug delivery system delivers therapeutic agent for about 3–7 days.

18. The method of claim 16 wherein the drug delivery system delivers therapeutic agent for at least about 7 days.

19. The method of claim 18 wherein the drug delivery system delivers therapeutic agent for about 14–30 days.

20. The method of claim 18 wherein the drug delivery system delivers therapeutic agent for about 30–90 days.

21. The method of claim 1 wherein the disease is periodontal disease.

22. The method of claim 21 wherein the therapeutic agent is an anti-inflammatory agent administered within the range of about 5–50 µg/day, for a time period of 7–90 days.

23. The method of claim 21 wherein the therapeutic agent is a bone and tissue growth factor administered within the range of about 5–50 µg/day, for a time period of 7–90 days.

24. The method of claim 21 wherein the therapeutic agent is an anti-infective agent having an MIC or MBC value of less than about 5 µg/ml for the bacterial species of interest and is administered within the range of about 5–25 µg/day, for a time period of 3–14 days.

25. The method of claim 1 wherein the disease is acute inflammation and the therapeutic agent is an anti-inflammatory agent.

26. The method of claim 25 wherein the anti-inflammatory agent is administered within the range of about 5–50 µg/day, for a time period of 3–14 days.

27. The method of claim 25 wherein the disease further comprises chronic inflammation and the anti-inflammatory agent is administered within the range of about 5–50 µg per day for about 5–10 days and about 2–25 µg thereafter for at least one month.

28. The method of claim 1 wherein the disease is chronic inflammation.

29. The method of claim 28 wherein the therapeutic agent is an anti-inflammatory agent administered within the range of about 5–50 µg/day, for a time period of 14–90 days.

30. The method of claim 1 wherein the disease is infection or susceptibility to infection.

31. The method of claim 30 wherein the therapeutic agent is an anti-infective agent for treating or preventing the infection and is administered within the range of about 5–50 µg/day, for a time period of 3–30 days.

32. The method of claim 1 wherein the disease is associated with pain and the therapeutic agent is a pain management medication and is administered within the range of about 5–50 µg/day, for a time period of 3–30 days.

33. The method of claim 1 wherein the disease is associated with pain and the therapeutic agent is an anti-inflammatory agent and is administered within the range of about 5–50 µg/day, for a time period of 3–30 days.

34. The method of claim 1 wherein the disease is tissue or bone loss and the therapeutic agent is a tissue or bone growth factor or agent that promotes bone or tissue regeneration administered within the range of about 2–50 µg/day, for a time period of 7–90 days.

35. The method of claim 1 which further comprises treating the patient with a device for facilitating tooth movement or providing orthodontic support by placing the device within the orofacial environment, and the therapeutic agent is a bone alteration agent and is administered within the range of about 2–50 µg/day, for a time period of about 7–60 days.

36. The method of claim 1 wherein the disease is cancer and the therapeutic agent is an antineoplastic agent administered within the range of about 5–50 µg/day, for a time period of 7–30 days.

37. The method of claim 1 wherein the disease is chemotherapy or radiotherapy induced oral mucositis and the therapeutic agent is an anti-inflammatory agent administered within the range of about 5–50 µg/day, for a time period of 7–30 days.

38. The method of claim 13 wherein the therapeutic agent is an anti-inflammatory agent and is administered within the range of about 5–50 µg/day.

39. The method of claim 13 wherein the therapeutic agent is a bone alteration agent and is administered within the range of about 5–50 µg/day.

40. The method of claim 13 wherein the therapeutic agent is an anti-infective agent and is administered within the range of about 5–50 µg/day.

41. The method of claim 40 wherein the therapeutic agent has a minimum inhibitory concentration or minimum bactericidal concentration of less than about 5 µ/ml and is administered within the range of about 5–25 µg/day.

42. The method of claim 13 wherein the therapeutic agent is a pain management medication and is administered within the range of about 5–50 µg/day.

43. The method of claim 13 wherein the therapeutic agent is a tissue or bone growth factor and is administered within the range of about 2–50 µg/day.

44. The method of claim 13 wherein the therapeutic agent is an antineoplastic agent and is administered within the range of about 5–50 µg/day.

45. The method of claim 13 wherein the therapeutic agent is a bone alteration agent and is administered within the range of about 2–50 µg/day.

46. The method of claim 13 wherein the therapeutic agent is a thyroid drug and is administered within the range of about 5–50 µg per day.

47. A method of treating disease in or originating in the orofacial environment in a patient comprising the step of administering a drug delivery system within orofacial tissue, wherein the system comprises a semi-solid or solid depot and a therapeutically effective amount of an anti-inflammatory agent contained therein, and wherein the anti-inflammatory agent comprises about 30–95 wt% of the depot.

48. The method of claim 47 wherein the system is implanted by a punch biopsy procedure, inserted with a trocar, inserted after a surgical incision or implanted by a surgical incision.

49. The method of claim 47 which further comprises administering one or more additional therapeutic agents selected from the group consisting of anti-infective agents, tissue and bone growth factors, pain management medication, antineoplastic agents, bone alteration agents, thyroid drugs, and combinations thereof.

50. The method of claim 49 wherein the one or more additional therapeutic agents are contained within the drug delivery system.

51. The method of claim 49 wherein the one or more additional therapeutic agents are contained within additional drug delivery systems, each comprising a semi-solid or solid depot and a therapeutically effective amount of the therapeutic agent contained therein, and having a size within the range of about 0.03–17 mm$^3$.

52. The method of claim 47 wherein the anti-inflammatory agent is administered within the range of about 5–50 µg/day.

53. The method of claim 47 wherein the drug delivery system delivers the anti-inflammatory agent for at least about 3 days.

54. The method of claim 47 wherein the disease is periodontal disease.

55. The method of claim 47 wherein the disease is acute inflammation.

56. The method of claim 55 wherein the disease further comprises chronic inflammation and the anti-inflammatory agent is administered within the range of about 5–50 µg per day for about 5–10 days and about 2–25 µg thereafter for at least one month.

57. The method of claim 47 wherein the disease is chronic inflammation.

58. The method of claim 47 wherein the disease is associated with pain.

59. The method of claim 47 wherein the anti-inflammatory agent is dexamethasone.

60. The method of claim 47 wherein the disease is thyroid disease.

61. A drug delivery system configured to be positioned within orofacial tissue comprising a semi-solid or solid depot and at least one therapeutic agent contained therein, and having a size within the range of about 0.03–17 mm$^3$, and wherein the therapeutic agent comprises about 30–95 wt% of the depot.

62. The drug delivery system of claim 61 wherein the depot is biodegradable.

63. The drug delivery system of claim 61 wherein the depot is non-biodegradable.

64. The drug delivery system of claim 61 wherein the depot is a monolith.

65. The drug delivery system of claim 61 wherein the depot is a reservoir.

66. The drug delivery system of claim 61 wherein the depot is a sponge.

67. The drug delivery system of claim 61 wherein the therapeutic agent comprises about 50–95 wt% of the depot.

68. The drug delivery system of claim 61 which comprises about 450–4500 µg of the therapeutic agent.

69. The drug delivery system of claim 68 which comprises about 35–1500 µg of the therapeutic agent.

70. The drug delivery system of claim 61 wherein the therapeutic agent is selected from the group consisting of anti-inflammatory agents, anti-infective agents, tissue and bone growth factors, pain management medication, antineoplastic agents, bone alteration agents, thyroid drugs, and combinations thereof.

71. The drug delivery system of claim 70 wherein the anti-inflammatory agent is a steroidal anti-inflammatory agent selected from the group consisting of alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluorometholone acetate, flurandrenolide, halcinonide, medrysone; methylprednisone suleptanate, pamidronate, paramethasone, prednisolone, nilutamide, triamcinelone, and combinations thereof.

72. The drug delivery system of claim 71 wherein the anti-inflammatory agent is dexamethasone.

73. The drug delivery system of claim 70 wherein the anti-infective agent has a minimum inhibitory concentration or minimum bactericidal concentration of less than about 5 μg/ml.

74. The drug delivery system of claim 70 wherein the tissue and bone growth factors are selected from the group consisting of growth hormones, alkaline phosphatase, dexamethasone, anti-degenerative agents, non-antimicrobial tetracyclines, matrix metalloendoproteinase inhibitors, 5-lipoxygenase inhibitors, nonsteroidal anti-inflammatory drugs, bisphosphonates, and combinations thereof.

75. The drug delivery system of claim 70 wherein the pain management medication is selected from the group consisting of anti-inflammatory agents, muscle relaxants, analgesics, anesthetics, and combinations thereof.

76. The drug delivery system of claim 70 wherein the antineoplastic agent is selected from the group consisting of carboplatin, cisplatin, cyclophosphamide, fluorouracil, leucovorin in combination with fluorouracil, leucovorin in combination with methotrexate, methotrexate, and combinations thereof.

77. The drug delivery system of claim 70 wherein the bone alteration agent is selected from the group consisting of prostaglandins.

78. The drug delivery system of claim 70 wherein the thyroid drug is selected from the group consisting of thyroxine, triiodothyronine, propylthiouracil, methimazole, and combinations thereof.

79. The drug delivery system of claim 61 which further comprises a membrane positioned adjacent the depot.

80. The drug delivery system of claim 61 which further comprises a backing layer.

81. The drug delivery system of claim 61 which further comprises an adhesive layer.

82. The drug delivery system of claim 61 which further comprises a release liner.

83. The drug delivery system of claim 61 which is spherical, cylindrical or flat.

84. The drug delivery system of claim 61 which provides a dosage of about 5–10 μg of therapeutic agent per day.

85. The drug delivery system of claim 84 which has a therapeutic agent loading of about 30–90 wt%.

86. The drug delivery system of claim 85 which has a density of about 0.9–1.3 g/cm$^3$.

87. The drug delivery system of claim 86 which has a therapeutic agent delivery duration of about 7–14 days.

88. The drug delivery system of claim 87 which is about 0.03–0.5 mm$^3$ in size.

89. The drug delivery system of claim 86 which has a therapeutic agent delivery duration of up to 1 month.

90. The drug delivery system of claim 89 which is about 0.13–1.1 mm$^3$ in size.

91. The drug delivery system of claim 86 which has a therapeutic agent delivery duration of up to 2 months.

92. The drug delivery system of claim 91 which is about 0.26–2.2 mm$^3$ in size.

93. The drug delivery system of claim 86 which has a therapeutic agent delivery duration of up to 3 months.

94. The drug delivery system of claim 93 which is about 0.38–3.3 mm$^3$ in size.

95. The drug delivery system of claim 61 which provides a dosage of about 10–25 μg of therapeutic agent per day.

96. The drug delivery system of claim 95 which has a therapeutic agent loading of about 50–70 wt%.

97. The drug delivery system of claim 96 which has a density of about 1 g/cm$^3$.

98. The drug delivery system of claim 97 which has a therapeutic agent delivery duration of up to 2 weeks.

99. The drug delivery system of claim 98 which is about 0.28–0.7 mm$^3$ in size.

100. The drug delivery system of claim 97 which has a therapeutic agent delivery duration of up to 1 month.

101. The drug delivery system of claim 100 which is about 0.6–1.5 mm$^3$ in size.

102. The drug delivery system of claim 97 which has a therapeutic agent delivery duration of up to 2 months.

103. The drug delivery system of claim 102 which is about 1.2–3 mm$^3$ in size.

104. The drug delivery system of claim 97 which has a therapeutic agent delivery duration of up to 3 months.

105. The drug delivery system of claim 104 which is about 1.8–4.5 mm$^3$ in size.

106. The drug delivery system of claim 61 which provides a dosage of about 25–50 μg of therapeutic agent per day.

107. The drug delivery system of claim 106 which has a therapeutic agent loading of about 30–90 wt%.

108. The drug delivery system of claim 107 which has a density of about 0.9–1.3 g/cm$^3$.

109. The drug delivery system of claim 108 which has a therapeutic agent delivery duration of up to 2 weeks.

110. The drug delivery system of claim 109 which is about 0.15–2.6 mm$^3$ in size.

111. The drug delivery system of claim 108 which has a therapeutic agent delivery duration of up to 1 month.

112. The drug delivery system of claim 111 which is about 0.64–5.6 mm$^3$ in size.

113. The drug delivery system of claim 108 which has a therapeutic agent delivery duration of up to 2 months.

114. The drug delivery system of claim 113 which is about 1.3–11 mm$^3$ in size.

115. The drug delivery system of claim 108 which has a therapeutic agent delivery duration of up to 3 months.

116. The drug delivery system of claim 115 which is about 1.9–17 mm$^3$ in size.

117. A drug delivery system configured to be positioned within orofacial tissue comprising a semi-solid or solid depot and about 35–4500 μg of a therapeutic agent contained therein, and having a size within the range of about 0.03–17 mm$^3$, and wherein the therapeutic agent comprises about 30–95 wt% of the depot.

118. The drug delivery system of claim 117 wherein the depot is a monolith, a reservoir or a sponge.

119. The drug delivery system of claim 117 wherein the therapeutic agent comprises about 50–95 wt% of the depot.

120. The drug delivery system of claim 117 wherein the therapeutic agent is selected from the group consisting of anti-inflammatory agents, anti-infective agents, tissue and bone growth factors, pain management medication, antineoplastic agents, bone alteration agents, thyroid drugs, and combinations thereof.

121. The drug delivery system of claim 120 wherein the anti-inflammatory agent is a steroidal anti-inflammatory agent selected from the group consisting of alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluorometholone acetate, flurandrenolide, halcinonide, medrysone; methylprednisone suleptanate, pamidronate, paramethasone, prednisolone, nilutamide, triamcinelone, and combinations thereof.

122. The drug delivery system of claim 121 wherein the anti-inflammatory agent is dexamethasone.

123. The drug delivery system of claim 120 wherein the anti-infective agent has a minimum inhibitory concentration or minimum bactericidal concentration of less than about 5 µg/ml.

124. The drug delivery system of claim 120 wherein the tissue and bone growth factors are selected from the group consisting of growth hormones, alkaline phosphatase, dexamethasone, anti-degenerative agents, non-antimicrobial tetracyclines, matrix metalloendoproteinase inhibitors, 5-lipoxygenase inhibitors, nonsteroidal anti-inflammatory drugs, bisphosphonates, and combinations thereof.

125. The drug delivery system of claim 120 wherein the pain management medication is selected from the group consisting of anti-inflammatory agents, muscle relaxants, analgesics, anesthetics, and combinations thereof.

126. The drug delivery system of claim 120 wherein the antineoplastic agent is selected from the group consisting of carboplatin, cisplatin, cyclophosphamide, fluorouracil, leucovorin in combination with fluorouracil, leucovorin in combination with methotrexate, methotrexate, and combinations thereof.

127. The drug delivery system of claim 120 wherein the bone alteration agent is selected from the group consisting of prostaglandins.

128. The drug delivery system of claim 120 wherein the thyroid drug is selected from the group consisting of thyroxine, triiodothyronine, propylthiouracil, methimazole, and combinations thereof.

129. The drug delivery system of claim 117 having a size within the range of 0.1–3 mm$^3$.

130. The drug delivery system of claim 129 which has a therapeutic agent delivery duration of about 1 week to 3 months.

131. The drug delivery system of claim 130 which has a therapeutic agent loading of about 50 wt%.

132. A method of treating disease in or originating in the orofacial environment in a patient comprising the step of (1) administering a first drug delivery system within orofacial tissue, wherein the system comprises a semi-solid or solid depot and a therapeutically effective amount of at least one therapeutic agent contained therein, and is within the range of about 0.03–17 mm$^3$ in size, wherein the therapeutic agent comprises about 30–95 wt% of the depot; and (2) administering one or more additional therapeutic agents; wherein the one or more additional therapeutic agents are contained within the first drug delivery system or are contained within additional drug delivery systems, each comprising a semi-solid or solid depot and a therapeutically effective amount of the therapeutic agent contained therein, and having a size within the range of about 0.03–17 mm$^3$. wherein the therapeutic agent comprises about 30–95 wt% of the depot.

133. The method of claim 132 wherein the additional therapeutic agents are selected from the group consisting of anti-inflammatory agents, anti-infective agents, tissue and bone growth factors, pain management medication, antineoplastic agents, bone alteration agents, thyroid drugs, and combinations thereof.

134. A method of treating disease in or originating in the orofacial environment in a patient comprising the step of(1) administering a drug delivery system within orofacial tissue, wherein the system comprises a semi-solid or solid depot and a therapeutically effective amount of an anti-inflammatory agent contained therein, wherein the therapeutic agent comprises about 30–95 wt% of the depot: and (2) administering one or more additional therapeutic agents selected from the group consisting of anti-infective agents, tissue and bone growth factors, pain management medication, antineoplastic agents, bone alteration agents, thyroid drugs, and combinations thereof.

135. The method of claim 134 wherein the one or more additional therapeutic agents are contained within the drug delivery system.

136. The method of claim 134 wherein the one or more additional therapeutic agents are contained within additional drug delivery systems, each comprising a semi-solid or solid depot and a therapeutically effective amount of the therapeutic agent contained therein, and having a size within the range of about 0.03–17 mm$^3$ and wherein the therapeutic agent comprises about 30–95 wt% of the depot.

* * * * *